(12) United States Patent
Tissenbaum et al.

(10) Patent No.: US 7,858,327 B2
(45) Date of Patent: Dec. 28, 2010

(54) METHODS OF IDENTIFYING LONGEVITY MODULATORS AND THERAPEUTIC METHODS OF USE THEREOF

(75) Inventors: Heidi A. Tissenbaum, Wayland, MA (US); Seung Wook Oh, Westborough, MA (US)

(73) Assignee: University of Massachusetts, Boston, MA (US)

( * ) Notice: Subject to any disclaimer, the term of this patent is extended or adjusted under 35 U.S.C. 154(b) by 505 days.

(21) Appl. No.: 10/746,910

(22) Filed: Dec. 23, 2003

(65) Prior Publication Data

US 2005/0037440 A1 Feb. 17, 2005

Related U.S. Application Data

(60) Provisional application No. 60/436,324, filed on Dec. 23, 2002.

(51) Int. Cl.
*A61K 49/00* (2006.01)
*G01N 33/53* (2006.01)
*G01N 33/567* (2006.01)

(52) U.S. Cl. .......................... 435/7.2; 424/9.2
(58) Field of Classification Search .................. None
See application file for complete search history.

(56) References Cited

U.S. PATENT DOCUMENTS 7,232,897 B2 * 6/2007 Hotamisligil et al. ........ 536/7.4

FOREIGN PATENT DOCUMENTS

WO     WO01/18549 A1 *  3/2001

OTHER PUBLICATIONS

Ip et al. Current Opinion in Cell Biology. 1998; 10:205-219.*
Isobe (Current Genomics, 2000, vol. 1, No. 1. pp. 1-10).*
Finkel et al. (Nature. vol. 408. Nov. 9, 2000, pp. 239-247).*
Weston et al. Current Opinion in Genetics and Development. 2002;12:14-21.*
Weston et al. (Current Opinion in Genetics & Development. 2002, 12:14-21).*
Kolodziejczyk et al (Current Biology. Aug. 21, 2001; 11(16): 1278-1282).*
Greer et al. (Oncogene. 2005; 24: 7410-7425).*
Aguirre et al. (Journal of Biological Chemistry. Mar. 24, 2000; 275(12):9047-9054).*
Wolff et al. (Experimental Gerontology. 2006; 41: 894-903).*
Villanueva et al. (EMBO 2001; 20(18): 5114-5128).*
Kawasaki et al. (EMBO. 1999; 18(13): 3604-3615).*
Villanueva et al. (EMBO. 2001; 20(18): 5115-5128).*
White (Am J Physiol Endocrinol Metab. 2002; 283: E413-E422).*
Cousin et al. (Endocrinology. 2001; 142(1): 229-240).*
Henderson et al. (Current Biology. 2001; 11: 1975-1980).*
Aguirre, Vincent et al, "The c-Jun NH$_2$-terminal Kinase Promotes Insulin Resistance during Association with Insulin Receptor Substrate-1 and Phosphorylation of Ser$^{307}$," *The Journal of Biological Chemistry*, vol. 275(12):9047-9054 (2000).
Apfeld, Javier et al, "Cell Nonautonomy of *C. elegans daf-2* Function in the Regulation of Diapause and Life Span," *Cell*, vol. 95:199-210 (1998).
Barsyte, Dalia et al, "Longevity and heavy metal resistance in *daf-2* and *age-1* long-lived mutants of *Caenorhabditis elegans*," *FASEB J.*, vol. 15:627-634 (2001).
Byrd, Dana Thyra et al, "UNC-16, a JNK-Signaling Scaffold Protein, Regulates Vesicle Transport in *C. elegans*," *Neuron*, vol. 32:787-800 (2001).
Cavigelli, Martin et al, "Induction of *c-fos* expression through JNK-mediated TCF/Elk-1 phosphorylation," *The EMBO Journal*, vol. 14(23):5957-5964 (1995).
Clancy, David J. et al, "Extension of Life-Span by Loss of CHICO, a *Drosophila* Insulin Receptor Substrate Protein," *Science*, vol. 292:104-106 (2001).
Dérijard, Benoit et al, "Independent Human MAP Kinase Signal Transduction Pathways Defined by MEK and MKK Isoforms," *Science*, vol. 267:682-685 (1995).
Dlakić, Mensur, "A new family of putative insulin receptor-like proteins in *C. elegans*," *Curr. Biol.*, vol. 12(5):R155-R157 (2002).
Feng, Jinliu et al, "Mitochondrial Electron Transport Is a Key Determinant of Life Span in *Caenorhabditis elegans*," *Developmental Cell*, vol. 1:633-644 (2001).
Friedman, David B. et al, "A Mutation in the *age-1* Gene in *Caenorhabditis elegans* Lengthens Life and Reduces Hermaphrodite Fertility," *Genetics*, vol. 118:75-86 (1988).
Gems, David et al, "Two Pleiotropic Classes of *daf-2* Mutation Affect Larval Arrest, Adult Behavior, Reproduction and Longevity in *Caenorhabditis elegans*," *Genetics*, vol. 150:129-155 (1998).
Gerisch, Birgit et al, "A Hormonal Signaling Pathway Influencing *C. elegans* Metabolism, Reproductive Development, and Life Span," *Developmental Cell*, vol. 1:841-851 (2001).

(Continued)

*Primary Examiner*—Scott Long
(74) *Attorney, Agent, or Firm*—Nelson Mullins Riley & Scarborough LLP; Debra J. Milasincic, Esq.; Cynthia L. Kanik

(57) ABSTRACT

The present invention is based at least in part on the discovery of a role for the JNK signaling pathway in longevity. In particular, the present inventors have shown that modulation of the c-jun N-terminal kinase (JNK) signaling pathway in an organism, optionally in combination with modulation of the insulin receptor (IR) signaling pathway, can enhance longevity in an organism. Accordingly, the present invention features methods of identifying modulators of longevity in assays featuring organisms and/or cells having either a functional or deregulated JNK signaling pathway and, optionally, a functional or deregulated IR signaling pathway. Also featured is an in vitro method of identifying an agent capable of enhancing longevity featuring an assay composition having a JNK signaling pathway molecule and insulin signaling pathway molecule. Further featured are therapeutic methods for the use of JNK signaling pathway modulators to enhance longevity.

10 Claims, 18 Drawing Sheets

OTHER PUBLICATIONS

Gil, Elad B. et al, "Regulation of the insulin-like developmental pathways of *Caenorhabditis elegans* by a homolog of the *PTEN* tumor suppressor gene," *Proc. Natl. Acad. Sci. USA*, vol. 96:2925-2930 (1999).

Hirosumi, J. et al. "A central role for JNK in obesity and insulin resistance," *Nature*, vol. 420(6913):333-336 (2002).

Holzenberger, M. et al, "IGF-1 receptor regulates lifespan and resistance to oxidative stress in mice," *Nature*, vol. 421(6919):182-187 (2003).

Honda, Yoko et al, "The *daf-2* gene network for longevity regulates oxidative stress resistance and Mn-superoxide dismutase gene expression in *Caenorhabditis elegans*," *FASEB J.*, vol. 13:1385-1393(1999).

Jia, Kailiang et al, "DAF-9, a cytochrome P450 regulating *C. elegans* larval development and adult longevity," *Development*, vol. 129:221-231 (2002).

Kawasaki, Masato et al, "A *Caenorhabditis elegans* JNK signal transduction pathway regulates coordinated movement via type-D GABAergic motor neurons," *The EMBO Journal*, vol. 18(13):3604-3615 (1999).

Kenyon, Cynthia, "Environmental Factors and Gene Activities That Influence Life Span," *C. Elegans II*, Cold Spring Harbor Laboratory Press, Riddle, Donald L. et al, eds., Ch. 28 (1997).

Kido, Yoshiaki et al, "The Insulin Receptor and Its Cellular Targets," *The Journal of Clinical Endocrinology & Metabolism*, vol. 86(3):972-979 (2001).

Kimura, K.D. et al, "daf-2, an insulin receptor-like gene that regulates longevity and diapause in *Caenorhabditis elegans*," *Science*, vol. 277(5328):942-946 (1997).

Koga, Makoto et al, "A *Caenorhabditis elegans* MAP kinase kinase MEK-1, is involved in stress responses," *The EMBO Journal*, vol. 19(19):5148-5156 (2000).

Lithgow, G.J. et al, "Stress resistance as a determinate of *C. elegans* lifespan," *Mech. Ageing Dev.*, vol. 123(7):765-771 (2002).

Lithgow, G.J. et al, "Thermotolerance of a long-lived mutant of *Caenorhabditis elegans*," *J. Gerontol.*, vol. 49(6):B270-B276 (1994).

Lithgow, Gordon J. et al, "Thermotolerance and extended life-span conferred by single-gene mutations and induced by thermal stress," *Proc. Natl. Acad. Sci. USA*, vol. 92:7540-7544 (1995).

Maehama, Tomohiko et al, "The Tumor Suppressor, PTEN/MMAC1, Dephosphorylates the Lipid Second Messenger, Phosphatidylinositol 3,4,5-Trisphosphate," *The Journal of Biological Chemistry*, vol. 273(22):13375-13378 (1998).

Mihaylova, Valia T. et al, "The PTEN tumor suppressor homolog in *Caenorhabditis elegans* regulates longevity and dauer formation in an insulin receptor-like signaling pathway," *Proc. Natl. Acad. Sci. USA*, vol. 96:7427-7432 (1999).

Morris, Jason Z. et al, "A phosphatidylinositol-3-OH kinase family member regulating longevity and diapause in *Caenorhabditis elegans*," *Nature*, vol. 382:536-539 (1996).

Murakami, Shin et al, "A Genetic Pathway Conferring Life Extension and Resistance to UV Stress in *Caenorhabditis elegans*," *Genetics*, vol. 143:1207-1218 (1996).

Ogg, Scott et al, "The *C. elegans* PTEN Homolog, DAF-18, Acts in the Insulin Receptor-like Metabolic Signaling Pathway," *Molecular Cell*, vol. 2:887-893 (1998).

Paradis, Suzanne et al, "A PDK1 homolog is necessary and sufficient to transduce AGE-1 PI3 kinase signals that regulate diapause in *Caenorhabditis elegans*," *Genes & Development*, vol. 13:1438-1452(1999).

Paradis, Suzanne et al. "*Caenorhabditis elegans* Akt/PKB transduces insulin receptor-like signals from AGE-1 PI3 kinase to the DAF-16 transcription factor," *Genes & Development*, vol. 12:2488-2498 (1998).

Pierce, Sarah B. et al, "Regulation of DAF-2 receptor signaling by human insulin and ins-1, a member of the unusually large and diverse *C. elegans* insulin gene family," *Genes & Development*, vol. 15:672-686 (2001).

Tatar, M. et al, "Slow aging during insect reproductive diapause: why butterflies, grasshoppers and flies are like worms," *Experimental Gerontology*, vol. 36:723-738 (2001).

Tissenbaum, Heidi A. et al, "Model Organisms as a Guide to Mammalian Aging," *Developmental Cell*, vol. 1:9-19 (2002).

Tissenbaum, Heidi A. et al, "An Insulin-like Signaling Pathway Affects Both Longevity and Reproduction in *Caenorhabditis elegans*," *Genetics*, vol. 148:703-717 (1998).

Tournier, Cathy et al, "Mitogen-activated protein kinase kinase 7 is an activator of the c-Jun $NH_2$-terminal kinase," *Proc. Natl. Acad. Sci. USA*, vol. 94:7337-7342 (1997).

Villanueva, Alberto et al, "*jkk-1* and *mek-1* regulate body movement coordination and response to heavy metals through jnk-1 in *Caenorhabditis elegans*," *The EMBO Journal*, vol. 20(18):5114-5128 (2001).

Weston, Claire R. et al, "The JNK signal transduction pathway," *Current Opinion in Genetics & Development*, vol. 12:14-21 (2002).

Wolkow, Catherine A. et al, "Insulin Receptor Substrate and p55 Orthologous Adaptor Proteins Function in the *Caenorhabditis elegans daf-2*/Insulin-like Signaling Pathways," *The Journal of Biological Chemistry*, vol. 277(51):49591-49597 (2002).

Yasuda, Jun et al, "The JIP Group of Mitogen-Activated Protein Kinase Scaffold Proteins," *Molecular and Cellular Biology*, vol. 19(10):7245-7254 (1999).

Al-Regaiey, Khalid A. et al., "Long-Lived Growth Hormone Receptor Knockout Mice: Interaction of Reduced Insulin-Like Growth Factor I/Insulin Signaling and Caloric Restriction," *Endocrinology*, vol. 146(2):851-860 (2005).

Barbieri, Michelangela et al., "Insulin/IGF-I-signaling pathway: an evolutionarily conserved mechanism of longevity from yeast to humans," *Am. J. Physiol. Endocrinol. Metab.*, vol. 285:E1064-E1071 (2003).

Blüher, Matthias et al., "Extended Longevity in Mice Lacking the Insulin Receptor in Adipose Tissue," *Science*, vol. 299:572-574 (2003).

Driver, Christopher, "An Hypothesis Concerning Control Networks and Aging in *Drosophila melanogaster* and *Caenorhabditis elegans*," *J. Amer. Aging Assoc.*, vol. 24:173-178 (2001).

Klöting, Nora et al., "Extended longevity and insulin signaling in adipose tissue," *Experimental Gerontology*, vol. 40:878-883 (2005).

Wang, Meng C. et al., "JNK Signaling Confers Tolerance to Oxidative Stress and Extends Lifespan in *Drosophila*," *Developmental Cell*, vol. 5:811-816 (2003).

\* cited by examiner

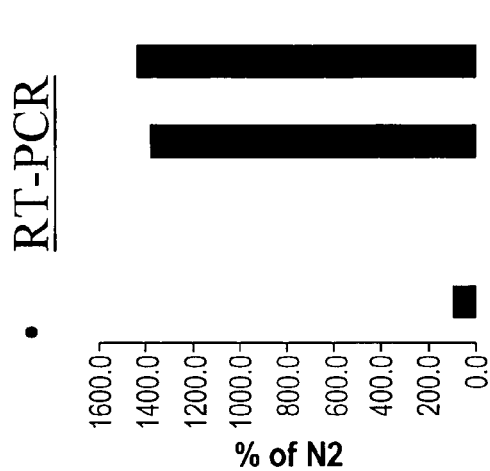
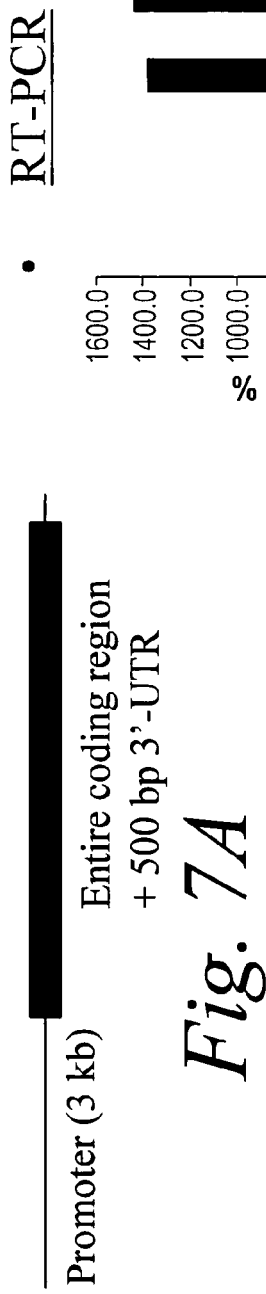
*Fig. 7A*
*Fig. 7B*
*Fig. 7C*

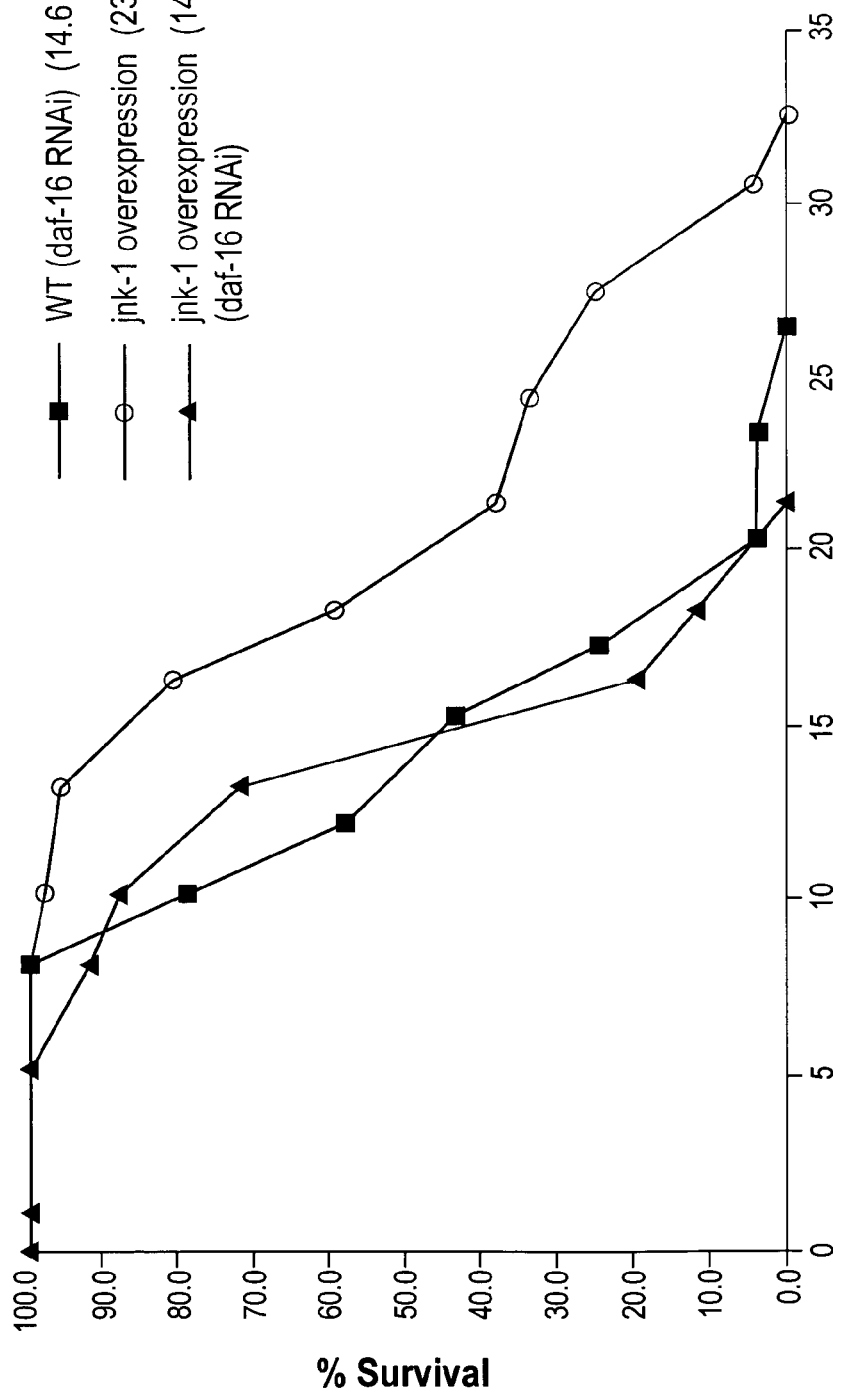

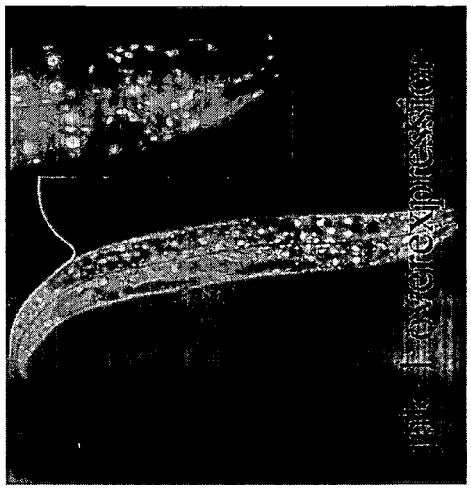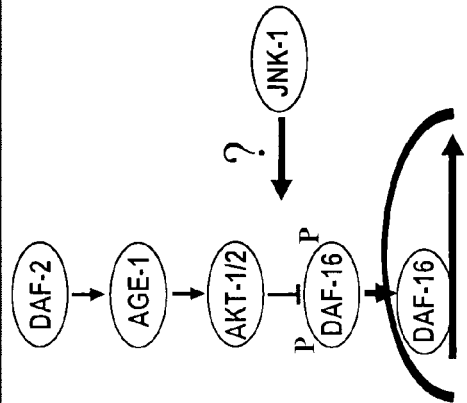
*Fig. 10C*
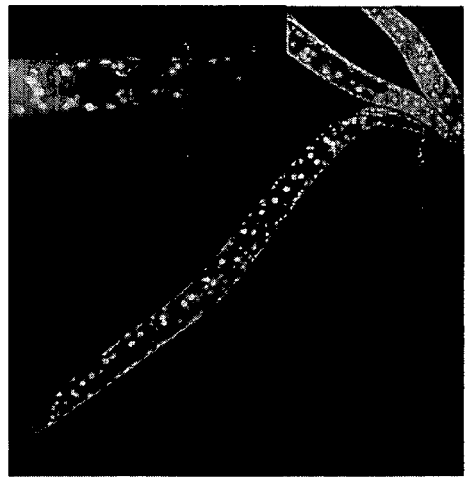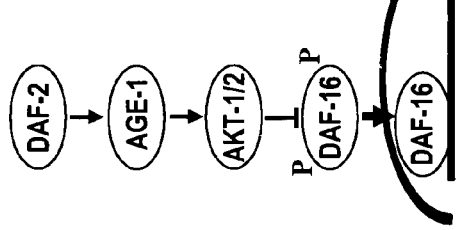
*Fig. 10B*
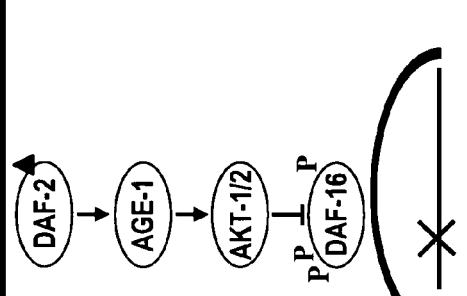
*Fig. 10A*

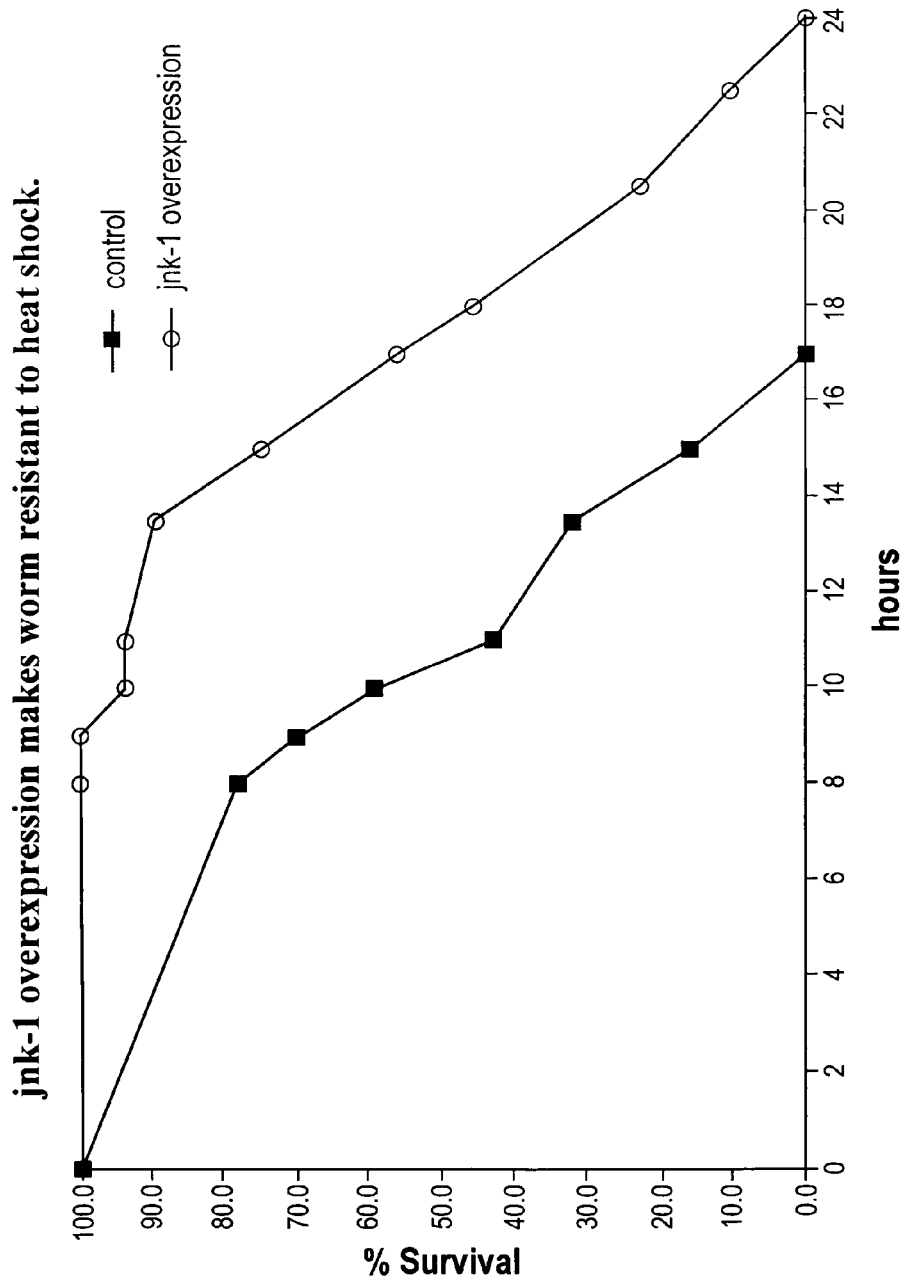

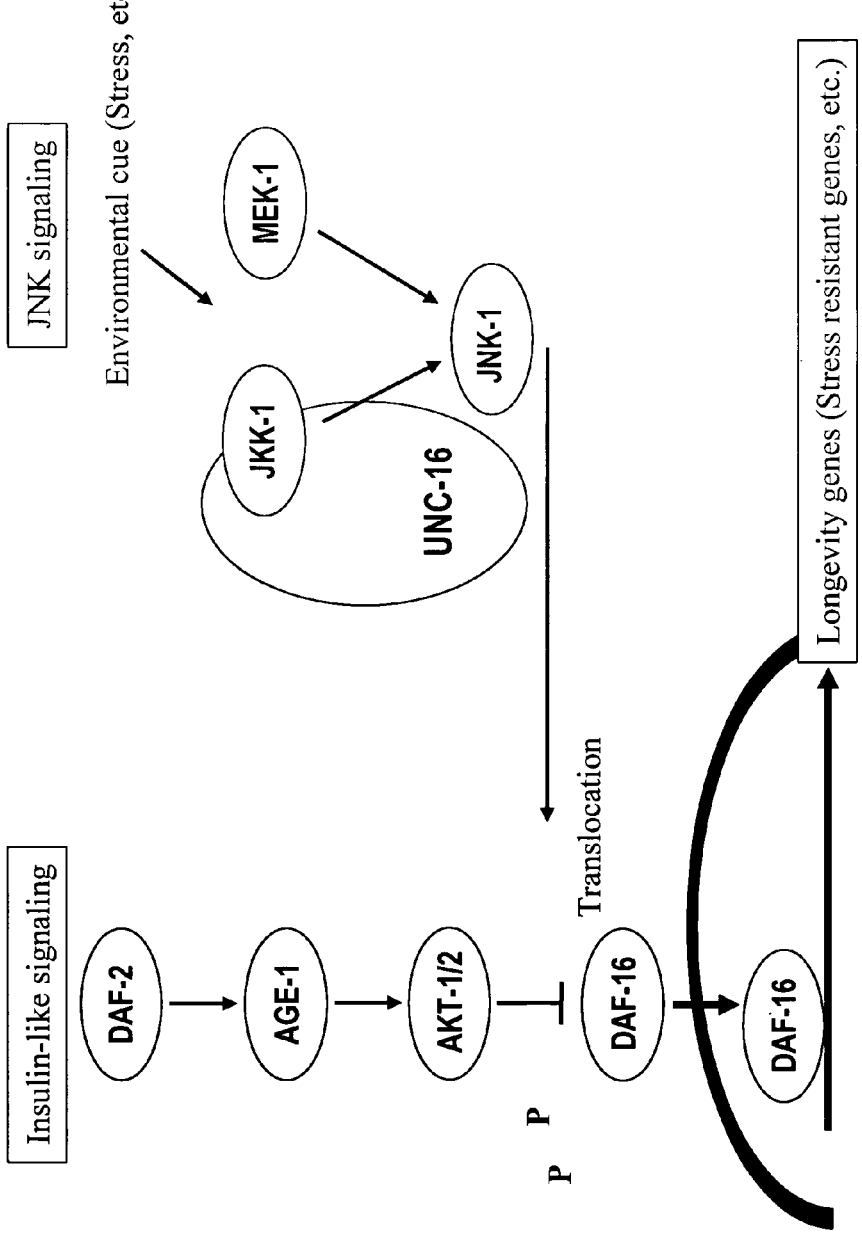
Fig. 13 Model: JNK signaling pathway can regulate lifespan by modulating nuclear translocation of DAF-16.

METHODS OF IDENTIFYING LONGEVITY MODULATORS AND THERAPEUTIC METHODS OF USE THEREOF

RELATED APPLICATIONS

This patent application claims the benefit of U.S. Provisional Patent Application Ser. No. 60/436,324, entitled "Methods of Identifying Longevity Modulators and Therapeutic Methods of Use Thereof", filed Dec. 23, 2002. The entire contents of the above-referenced provisional patent application are incorporated herein by this reference.

GOVERNMENT RIGHTS

This invention was made at least in part with government support under grant no. DK32520-19 awarded by the National Institutes of Health. The government may have certain rights in this invention.

BACKGROUND OF THE INVENTION

Aging in mammals can have a profound deleterious effect on brain function that manifests primarily in deficits of cognitive and motor function. Longevity genes are thus of obvious interest and importance, both for their life-extension potential and the possibility of their contributing to the enhancement of the quality of life, particularly later during the lifespan. However, very few of these genes have been identified and even less is understood about how these genes act to prevent aging and promote life extension.

Accordingly, there exists the need to discover genes whose function is associated with life-extension. Such genes and their products would be useful in the screening for anti-aging agents and would serve as key targets in various anti-aging therapies. Indeed, an understanding of the mechanisms underlying aging will ultimately provide us with the tools necessary to alleviate these deficits in the aged population and thereby prolong the independence of the elderly.

The roundworm *C. elegans* is a valuable invertebrate model system to study aging owing to its short, reproducible life span and its amenability to genetic and molecular analysis. Further, as the entire *C. elegans* genome is sequenced, it is feasible to envisage a comprehensive identification of all the genes that affect aging in this organism. In molecular genetics, extended life span remains one of the best indicators that an intervention in an aging process has been made. The life span of *C. elegans* is easily extendable by various genetic, transgenic, and pharmacologic means, and the isolation of long-lived variants in *C. elegans* has begun to provide clear insights into the putative mechanisms and consequences of aging in the CNS.

The main pathway that regulates life span in *C. elegans* is an insulin-like signaling pathway. Mutations in genes in this pathway can increase, decrease, or have no effect on life span. Interestingly, several of these genes were first isolated based on their effects on development. The normal lifecycle of *C. elegans* follows development from an egg, through four larval stages, and a final molt into a fertile, adult hermaphrodite. When nutrition is low or population density is high, the worms can undergo an alternative developmental program to form "dauer" larvae (Cassada R. C. & Russell R. (1975) *Dev. Biology* 46:326-342). The dauer larvae is a diapause stage that does not feed or reproduce, is stress resistant and is apparently non-aging, wherein worms can remain as dauer larvae for months (Klass M. R. & Hirsh D. I. (1976) *Nature* 260:523-525). When conditions improve, worms can re-enter the life cycle and develop into a normal reproductive hermaphrodite. The dauer formation genes (daf), or genes that determine the decision to progress through development normally or undergo dauer formation, were first isolated on the basis that they either promote dauer arrest under plentiful growth conditions (dauer constitutive) or prevent dauer formation under crowded conditions (dauer defective) (Riddle D. L. et al. in *C. elegans* II, (1997) 739-768, Cold Spring Harbor Laboratory Press). Several of these genes, including daf-2, age-1 and daft 6, were subsequently identified as part of an insulin-like signaling pathway, supporting the idea that genes that affect entry into the dauer stage also affect life span in *C. elegans*.

The insulin-like signaling pathway in *C. elegans* contains numerous genes, many of which were isolated originally through their effects on dauer formation. Of the 37 insulin family members that have been identified in the *C. elegans* genome, only one insulin receptor-like gene, daf-2 (Pierce S. B. et al. (2001) *Genes and Dev.* 15:672-686; Gregoire F. M. et al. (1998). *Biochem Biophys Res Com.* 249:385-390) has been clearly identified. DAF-2 highly resembles both the mammalian insulin receptor and the related insulin growth factor-1 receptor (IGF1-R) (Kimura K. et al. (1997) *Science* 277:942-946). The ligand that binds to the DAF-2 receptor is not yet known. Activation of the insulin-like receptor DAF-2 by the as yet unidentified ligand leads to activation of PI-3 kinase, which in turn results in the generation of phosphoinositide-3-phosphate ($PIP_3$). In mammalian systems, $PIP_3$ acts as an intracellular messenger to activate downstream kinases (Kido Y. et al. (2001) *J of Clin End and Met* 86: 972-979; Alessi, D. R. & Downes, C. P., (1998) *Biochim Biophys Acta* 1436: 151-164). In *C. elegans*, the catalytic subunit, p110, of PI-3 kinase is encoded by the age-1 gene (Morris J. Z. et al. (1996) *Nature* 382:536-539). Decrease in function mutations in either daf-2 or age-1 result in various phenotypes including constitutive dauer formation during development, fertility defects, resistance to stresses such as heat, oxidative damage and heavy metals, and extension of life span in adults (Lithgow G. J. et al., (1994) *J. Gerontol.* 49:B270-276; Lithgow G. J. et al., (1995) *PNAS USA* 92:7540-4; Murakami S. & Johnson T. E. A Genetics 143: 1207-1218; Honda Y. & Honda S., (1999) *FASED J* 13:1385-1393; Baryste D., (2001) *FasEB J* 15:627-634; Friedman D. B. & Johnson T. E., (1988) *Genetics* 118:75-86; Klass M. R., (1983) *Mech of Ageing and Dev.* 22:279-286). Another gene in the pathway, daf-18, encodes a homolog of the mammalian tumor suppressor PTEN phosphatase (Rouault J. P., (1999) *Curr Biology* 9:329-332; Ogg S. & Ruvkun G., (1998) *Mol Cell* 2:887-893; Mihaylova V. T. et al., (1999) *PNAS USA* 96:7427-7432; Gil E. B. et al. (1999) *PNAS USA* 96:2925-2930). DAF-18 functions to regulate the levels of $PIP_3$ by dephosphorylating the inositol ring in the third position (Maehama T. & Dixon J. E. (1998) *J Biol Chem* 273:13375-13378). Loss of function mutations in daf-18 result in a decrease in life span and suppression of both daf-2 and age-1 dauer phenotypes (Rouault J. P. (1999) *Curr Biol* 9:329-332; Ogg S. & Ruvkun G. (1998) *Mol Cell* 2:887-893; Mihaylova V. T. (1999) *PNAS USA* 96:7427-7432; Gil E. B. et al. (1999) *PNAS USA* 96:2925-2930.)

Downstream of age-1 are the kinases PDK-1, AKT-1, and AKT-2. The PDK-1 and AKT-1 kinases were identified in *C. elegans* as gain-of-function suppressors of the dauer-constitutive phenotype of age-1 mutants (Paradis S. & Ruvkun G. (1998) *Genes Dev* 12:2488-2498; Paradis S. (1999) *Genes Dev* 13:1438-1452). Similar to the phenotype observed for mutations in daf-2 and age-1, a reduction of function mutation in PDK-1 increases adult life span (Paradis S. (1999) *Genes Dev* 13:1438-1452). The final output of the pathway is daf-16, which encodes a homolog of the HNF-3/forkhead family of transcription factors (Kimura K. et al. (1997) *Science* 277:942-946; Ogg S. et al. (1997) *Nature* 389:994-9; Lin K. et al. (1997) *Science* 278:1319-1322). Null mutations of daf-16 decrease life span and completely suppress all phenotypes in double mutant combinations with daf-2 or age-1. Thus life span extension by either daf-2 or age-1 mutations requires a wild type daf-16 gene. Given that DAF-1 and AGE-1 proteins act to suppress the activity of DAF-16, it is believed that the lack of signaling in daf-2 or age-1 mutants causes increased activity of DAF-16, ultimately leading to the observed phenotypes. The final targets of DAF-16 in this pathway remain unknown but are presumed to regulate metabolism and fat storage (Kimura K. et al. (1997) *Science* 277:942-946; Lithgow G. J. et al. (1995) *PNAS USA* 92:7540-4).

In order to elucidate fully the mechanisms underlying aging, it will be critical to identify all pathways that play a role in its regulation. Importantly, genetic analysis of the DAF-2 insulin-like receptor strongly indicates that other genes are involved in signaling downstream of daf-2 (Ogg S. & Ruvkun G. (1998) *Mol Cell* 2:887-893). This is due to the fact that a loss of function mutation in the daf-16 forkhead transcription factor completely suppresses all of the phenotypes of a loss of function mutation in either daf-2 or age-1 (Kenyon, C. in *C. elegans* II (1997) 791-813, Cold Spring Harbor Press; Tissenbaum H. A. & Ruvkun G. (1998) *Genetics* 148:703-717)). However, loss of function mutations in daf-18 as well as gain of function mutation in either akt-1 and pdk-1 only suppress a subset of the phenotypes associated with the daf-2 and age-1 loss of function mutations (Paradis S. & Ruvkun G. (1998) *Genes Dev* 12:2488-2498; Paradis S. et al. *Genes Dev* 13:1438-1452; Ogg S. & Ruvkun G. (1998) *Mol Cell* 2:887-893). These data indicate that an additional pathway(s) is active downstream of daf-2 but upstream of daf-16. There exists, therefore, a clear need in the art for the elucidation of additional pathways involved in regulating aging.

Importantly, the influence of the insulin/IGF signaling pathway on lifespan has been conserved across large evolutionary distances. In the fruit fly *Drosophila*, reduced insulin/IGF signaling also mediates life-span extensions (Clancy D. J. (2001) *Science* 292:104-106; Tatar M. & Yin C. (2001) *Exp. Gerontol.* 36:723-738). This conservation indicates that certain physiological processes effecting life span are very ancient and strongly suggests that information on the aging of simple animals is likely to be important for mammalian aging. The study of development and longevity in *C. elegans* is thus expected to uncover critical new targets for insulin regulators in higher organisms and potential anti-aging targets for drug intervention in humans.

SUMMARY OF THE INVENTION

The present invention is based at least in part on the discovery of a role for the JNK signaling pathway in longevity. In particular, the present inventors have shown that modulation of the c-jun N-terminal kinase (JNK) signaling pathway in an organism, optionally in combination with modulation of the insulin receptor (IR) signaling pathway, can enhance longevity in an organism. Studies performed in the *C. elegans* model organism indicate that inhibition of JNK signaling, in particular, inhibition of JNK enzymatic activity, decreases lifespan and that inhibition of other molecules in the JNK signaling pathway in combination with an inhibition of IR signaling can extend or decrease lifespan. Studies further indicate that enhancement of JNK signaling, in particular, overexpression of jnk-1, extends lifespan and that said extended lifespan is associated with DAF-16 localization to the nucleus.

Accordingly, the present invention features methods of identifying modulators of longevity in assays featuring organisms and/or cells having either a functional or deregulated JNK signaling pathway and, optionally, a functional or deregulated IR signaling pathway.

In one embodiment, the invention provides a method for identifying an agent capable of enhancing longevity, involving contacting an organism having a deregulated c-jun N-terminal kinse (JNK) signaling pathway and, optionally, a deregulated IR signaling pathway, with a test agent, wherein the the test agent is identified based on its ability to alter a phenotype associated with the deregulated signaling pathway(s) as compared to a suitable control.

In another embodiment, the invention provides a method for identifying an agent capable of enhancing longevity, involving contacting an organism having a deregulated c-jun N-terminal kinse (JNK) signaling pathway with a test agent, and identifying an agent based on its ability to alter a downstream indicator of the c-jun N-terminal kinse (JNK) signaling pathway as compared to a suitable control.

Also featured are cell-based assays for the identification of an agent capable of enhancing longevity. The invention features a method involving contacting a cell having a JNK signaling pathway, optionally in combination with an insulin receptor (IR) signaling pathway, with a test agent, and identifying the agent based on its ability to modulate the signaling pathway(s) by detecting a signaling pathway indicator(s).

Also featured is an in vitro method of identifying an agent capable of enhancing longevity. This method involves the steps of: (a) contacting a first assay composition with a test compound, wherein the assay composition comprises a JNK signaling pathway molecule; (b) detecting activity or expression of the JNK signaling pathway molecule; (c) contacting a second assay composition with the test compound, wherein the assay composition comprises an insulin signaling pathway molecule; and (d) detecting activity or expression of the insulin signaling pathway molecule, wherein the agent is identified based on its ability to modulate activity or expression of the JNK signaling pathway molecule and insulin signaling pathway molecule.

Further featured are therapeutic methods for use of JNK signaling pathway modulators in order to enhance longevity in a subject, for example, a human subject. In one embodiment, the invention features a method for enhancing longevity in a subject, involving administering to a subject in need of enhanced longevity a pharmacologically effective dose of an agent that modulates a JNK signaling pathway molecule, wherein the modulation of the JNK signaling pathway molecule in the subject enhances longevity.

Other features and advantages of the invention will be apparent from the following detailed description and claims.

BRIEF DESCRIPTION OF THE DRAWINGS

FIG. 7A is a schematic representation of genomic DNA that was amplified and injected into *C. elegans* to construct a jnk-1 overexpression transgenic strain.

FIG. 7B shows the results of genomic PCR analysis from a single-worm demonstrating the presence of extra copies of jnk-1 in a jnk-1 overexpression transgenic strain.

FIG. 7C shows the results of RT-PCR analysis of a jnk-1 overexpression transgenic strain demonstrating a 10-fold overexpression of jnk-1 and a bar graph quantitatively summarizing the data.

FIG. 9 is a graphical depiction of life span analysis of a transgenic *C. elegans* strain in which jnk-1 is overexpressed or in which both jnk-1 is overexpressed and daf-16 is knocked down by RNAi.

FIG. 10A is an image of GFP-tagged DAF-16 in a wild type *C. elegans* strain.

FIG. 10B is an image of GFP-tagged DAF-16 in a daf-2 mutant *C. elegans* strain.

FIG. 10C is an image of GFP-tagged DAF-16 in a jnk-1 overexpression *C. elegans* strain.

FIG. 12B is a graphical depiction of heat shock stress analysis of a jnk-1 overexpression *C. elegans* strain.

FIG. 13 is a model depicting the role of the JNK signaling pathway in life span, wherein JNK signaling can regulate life span by modulating nuclear translocation of DAF-16.

DETAILED DESCRIPTION OF THE INVENTION

Figure 1:
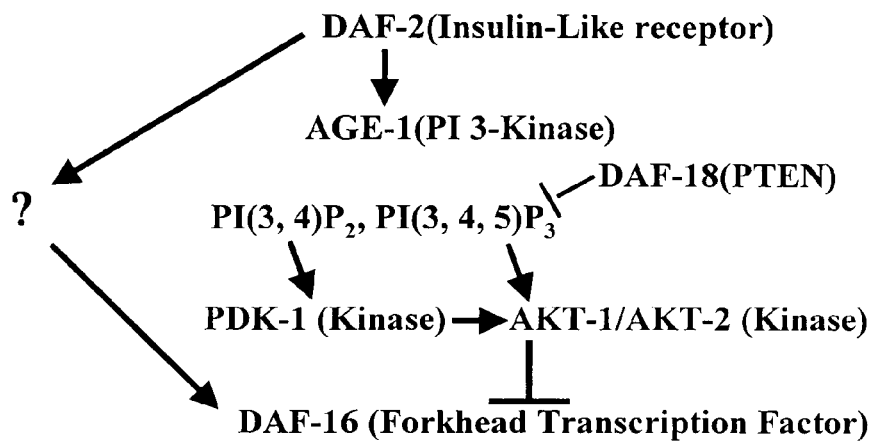
FIG. 1 is a schematic representation of the insulin receptor (IR) signaling pathway.

The present invention is based, at least in part, on the discovery of a central role for the JNK signaling pathway in controlling longevity. In particular, the invention is based on the discovery that members of the JNK signaling cascade are involved in either increasing or decreasing life span extension associated with reduction of function mutations in the insulin-like signaling pathway genes daf-2 and age-1 in *C. elegans*, and that overexpression of members of the JNK signaling cascade increases lifespan.

Accordingly, the invention features whole organism-based assays for the identification of an agent capable of enhancing longevity. In one aspect, the invention features a method for identifying an agent capable of enhancing longevity, involving: (a) contacting an organism having a deregulated c-jun N-terminal kinse (JNK) signaling pathway with a test agent, wherein a detectable phenotype is associated with the deregulated JNK signaling pathway; and (b) assaying for the ability of the test agent to effect the phenotype, wherein the agent is identified based on its ability to alter the phenotype as compared to a suitable control. A variation on this method involves (a) contacting an organism further having a deregulated insulin signaling pathway, wherein said detectable phenotype is associated with said deregulated JNK signaling pathway and said deregulated insulin signaling pathway, and (b) assaying for the ability of the test agent to effect the phenotype, wherein the agent is identified based on its ability to alter the phenotype as compared to a suitable control.

In preferred embodiments, the deregulated JNK signaling pathway molecule is selected from the group consisting of: UNC-16, MEK-1, JKK-1 and JNK-1, or a mammalian orthologue thereof. In further preferred embodiments, the deregulated insulin signaling pathway molecule is selected from the group consisting of DAF-2, AAP-1, IRS-1, AGE-1, PDK-1, AKT-1, AKT-1 and DAF-2, or a mammalian orthologue thereof.

In preferred embodiments the phenotypes include, but are not limited to, one or more of the following: increased or decreased life span, constitutive or defective dauer formation, increased or decreased body size, and increased or decreased stress resistance, e.g. oxidative stress, UV stress, hypoxic stress, heavy metal stress and heat stress.

In another aspect, the invention provides a method for identifying an agent capable of enhancing longevity, involving: (a) contacting an organism having a c-jun N-terminal kinase (JNK) signaling pathway with a test agent, and (b) assaying for the ability of the test agent to effect a downstream indicator of the c-jun N-terminal kinase (JNK) signaling pathway, wherein the agent is identified based on its ability to alter the indicator as compared to a suitable control. In one embodiment, the JNK signaling pathway is deregulated.

In preferred embodiments, the agent alters activity of the indicator, cellular localization, e.g. cytoplasmic to nuclear, of the indicator, and nucleic acid or polypeptide expression, e.g. rate of expression or steady state expression. In further preferred embodiments, the agent alters the post-translational modification state of the indicator, e.g., phosphorylation state. In still further preferred embodiments, the indicator is DAF-16 or superoxide dismutase, or a glucose transporter, e.g., glucose transporter 1 or glucose transporter 4.

In preferred embodiments, the organism is a nematode, e.g., *C. elegans* or a parasitic nematode.

The invention further features cell-based assays for the identification of an agent capable of enhancing longevity. In one aspect, the invention provides methods for identifying an agent that enhances longevity, involving (a) contacting a cell with a test agent, said cell having a JNK signaling pathway; (b) detecting an indicator of JNK signaling; and (c) identifying the agent based on its ability to modulate JNK signaling in said cell. In another aspect, the invention provides a method for identifying an agent that enhances longevity, comprising (a) contacting a cell with a test agent, said cell having a JNK signaling pathway and an insulin signaling pathway; (b) detecting an indicator of JNK signaling and insulin signaling; and (c) identifying the agent based on its ability to modulate JNK signaling and insulin signaling in said cell.

In one embodiment, the agent inhibits the signaling pathway(s), e.g., inhibits the insulin signaling pathway and the JNK signaling pathway. In another embodiment, the agent enhances the JNK signaling pathway and, optionally, inhibits the insulin signaling pathway.

In preferred embodiments, the cell is a mammalian cell, e.g. a human cell, a bacterial cell, a yeast cell, or is derived from a nematode.

In preferred embodiments, the indicator is selected from, but not limited to, one or more of the following: conversion of substrate to corresponding product catalyzed by a downstream enzyme in the pathway, activation or inhibition of a downstream enzyme in the pathway, a transcriptional event in the pathway, and activation or inhibition of a transcription factor regulated by the pathway.

In preferred embodiments, the indication involves an endogenous gene or protein, or a reporter gene or protein.

The invention further features an in vitro method of identifying an agent capable of enhancing longevity, involving: (a) contacting a first assay composition with a test compound, wherein the assay composition comprises a JNK signaling pathway molecule; (b) detecting activity or expression of the JNK signaling pathway molecule; (c) contacting a second assay composition with the test compound, wherein the assay composition comprises an insulin signaling pathway molecule; and (d) detecting activity or expression of the insulin signaling pathway molecule, wherein the agent is identified based on its ability to modulate activity or expression of the JNK signaling pathway molecule and insulin signaling pathway molecule.

In preferred embodiments, the deregulated JNK signaling pathway molecule is selected from the group consisting of: UNC-16, MEK-1, JKK-1 and JNK-1, or a mammalian orthologue thereof. In further preferred embodiments, the deregulated insulin signaling pathway molecule is selected from the group consisting of DAF-2, AAP-1, IRS, AGE-1, PDK-1, AKT-1, AKT-1 and DAF-2, or a mammalian orthologue thereof.

In further preferred embodiments, the assay composition is a cell-free extract, or purified proteins.

The invention further features a method for enhancing longevity in a subject, involving: (a) selecting a subject in need of enhanced longevity; and (b) administering to the subject a pharmacologically effective dose of an agent that modulates a JNK signaling pathway molecule, wherein the modulation of the JNK signaling pathway molecule in the subject enhances longevity.

In preferred embodiments, the agent modulates a JNK signaling pathway molecule selected from, but not limited to, the group consisting of: MAPKKKs, JNK, MKK4, MKK7 and JIF scaffold protein. In one embodiment, said agent increases the activity or expression of JNK. In another embodiment, said agent inhibits JNK. In further preferred embodiments, the agent inhibits an insulin signaling pathway molecule selected from, but not limited to, the group consisting of IR, IGF, IRS, PI3-K, PTEN phosphatase, PDK1, PKB and forkhead transcription factors, e.g. FKHR.

In further preferred embodiments, the subject is an aging or aged subject, a subject exhibiting at least one symptom of premature aging, or has an aging-associated disorder.

So that the invention may be more readily understood, certain terms are first defined.

"Longevity" and "life-extension", used interchangeably herein, also include delay and/or stabilizing the aging process. Preferably, the longevity is due to an extension of the mature life phase, as opposed to an extension of the immature life phase (i.e., delay in maturity).

A "function" of a polynucleotide can be on any level, including DNA binding, transcription, translation, processing and/or secretion of expression product, interaction (such as binding) of expression product with another moiety, and regulation (whether repression or de-repression) of other genes. It is understood that a life-extension polynucleotide or polypeptide includes fragments, or regions, of a polynucleotide or polypeptide, as long as the requisite life-extension phenotype is observed.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

A "gerontogene" is a gene, the alteration of which slow aging, extends lifespan and/or enhances late-life health. See e.g., Rattan (1985) *Bioessays* 2:226-228. Such genes can also been termed "longevity assurance genes" or "longevity associated genes" (both abbreviated "LAGs"). See e.g., D'Mello et al., (1994) *J. Biol. Chem.* 269:15451-15459.

The term "JNK signaling pathway" refers to the signaling pathway involving proteins (e.g., enzymes) and other non-protein molecules (e.g., precursors, substrates, intermediates or products), utilized in transmission of an intracellular signal from a cell membrane (e.g., from a cell surface receptor) to the nucleus, wherein such signal transmission involves at least c-jun N-terminal kinase (JNK). FIG. 1 includes a schematic representation of the JNK signaling pathway. Additional signaling molecules in the JNK signaling pathway in mammals, for example, include the MAP Kinase Kinase Kinases (MAPKKKs), JNK, MKK4, MKK7, and JIF scaffold protein. Such signaling molecules in *C. elegans*, for example, include, UNC-16, MEK-1, JKK-1, and c-jun N-terminal kinase-1 (JNK-1), (and the corresponding genes encoding these molecules, i.e., unc-16, mek-1, jkk-1 and jnk-1, respectively.

Figure 2:
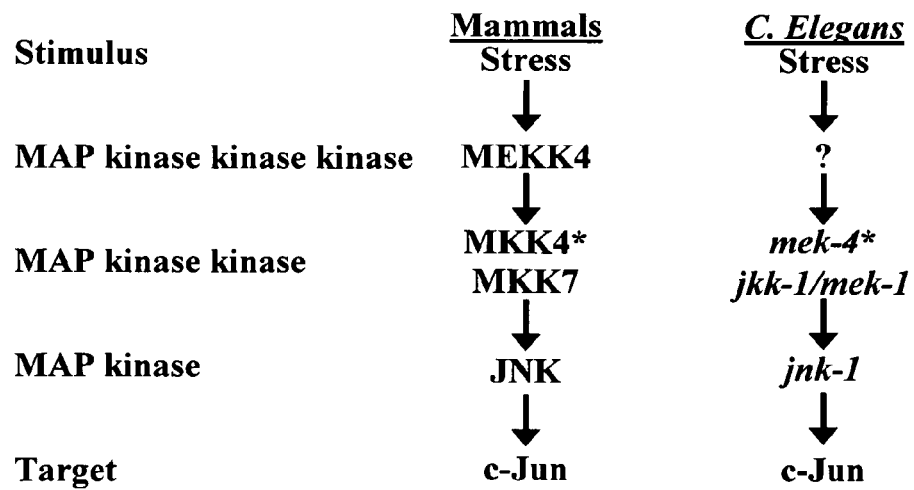
FIG. 2 is a schematic representation of the c-jun N-terminal kinase (JNK) signaling pathway.
Figure 3A:
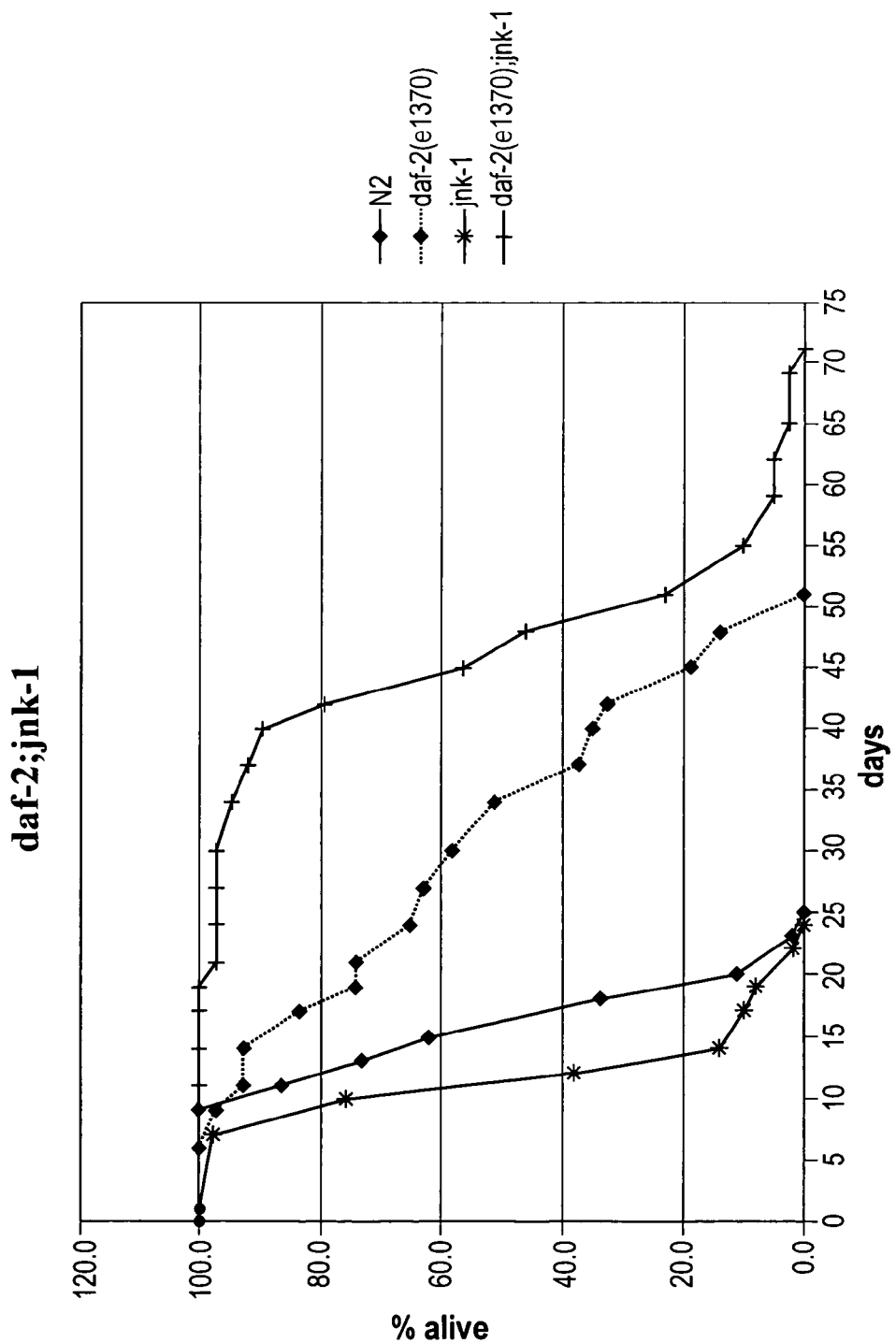
FIG. 3A-D is a graphical depiction of life span analysis of mutant *C. elegans* strains containing reduction of function mutations in jnk-1, unc-16, mek-1 and jkk-1 alone, and in combination with a reduction of function daf-2 mutation.
Figure 3B:
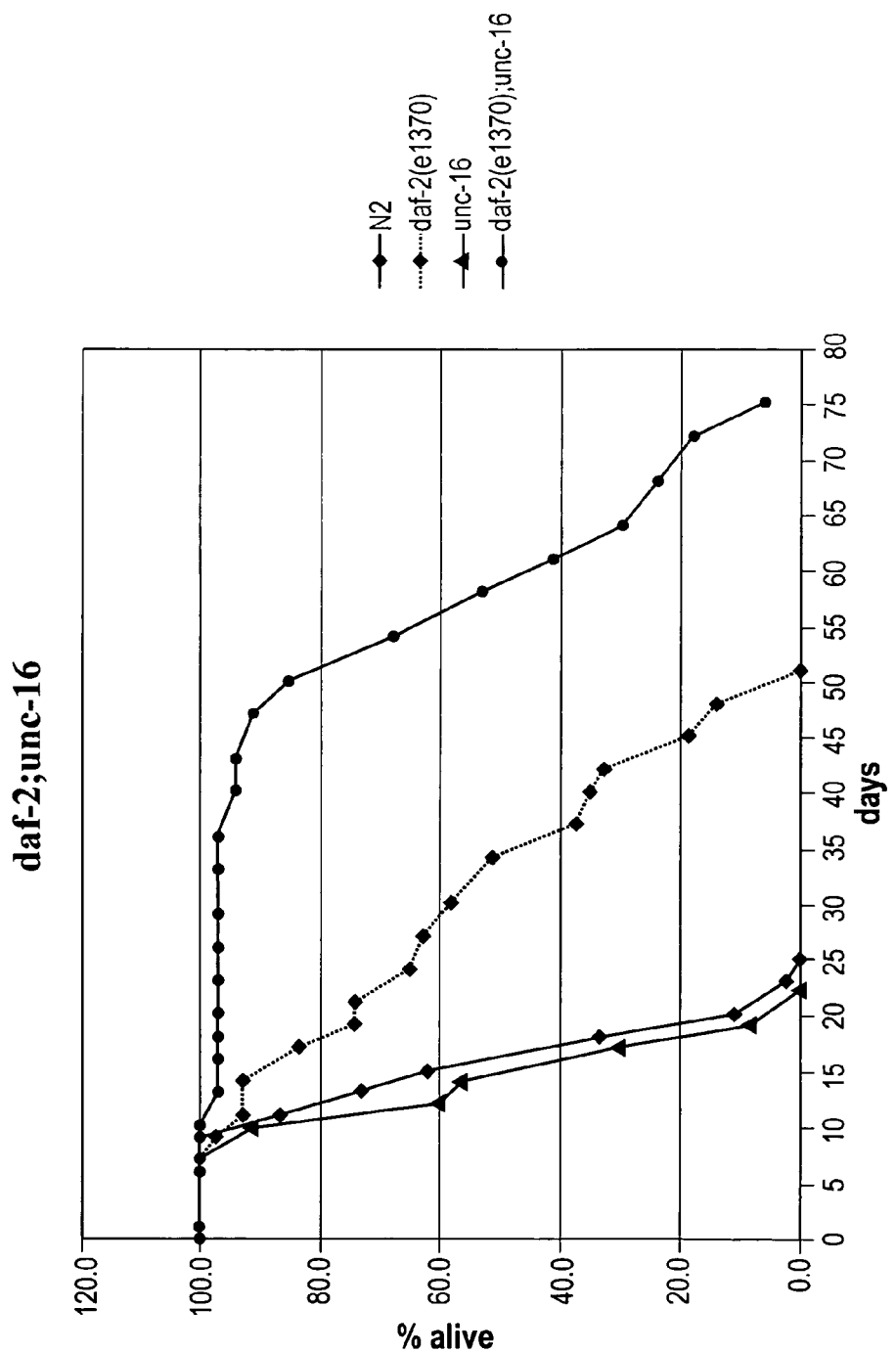
Figure 3C:
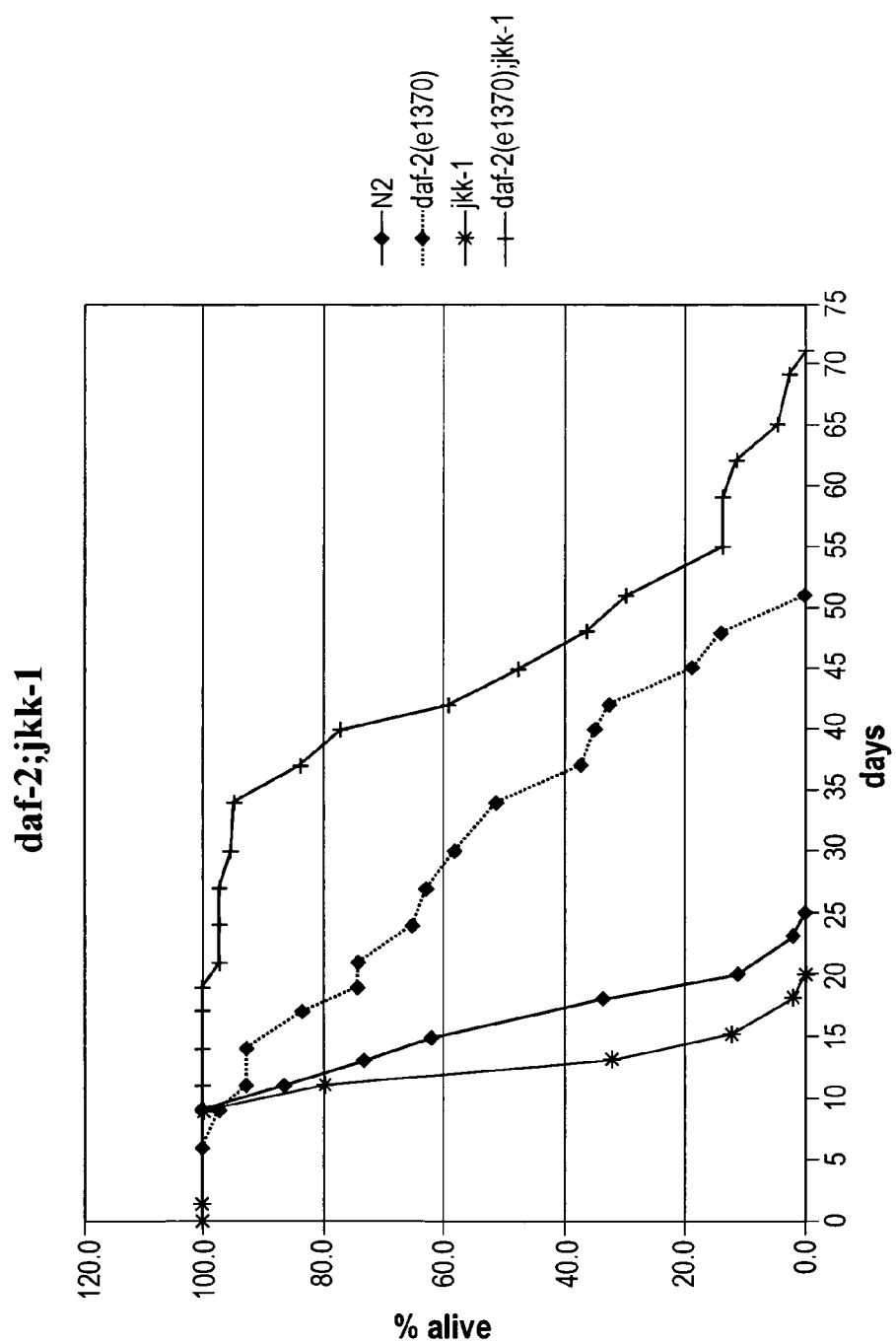
Figure 3D:
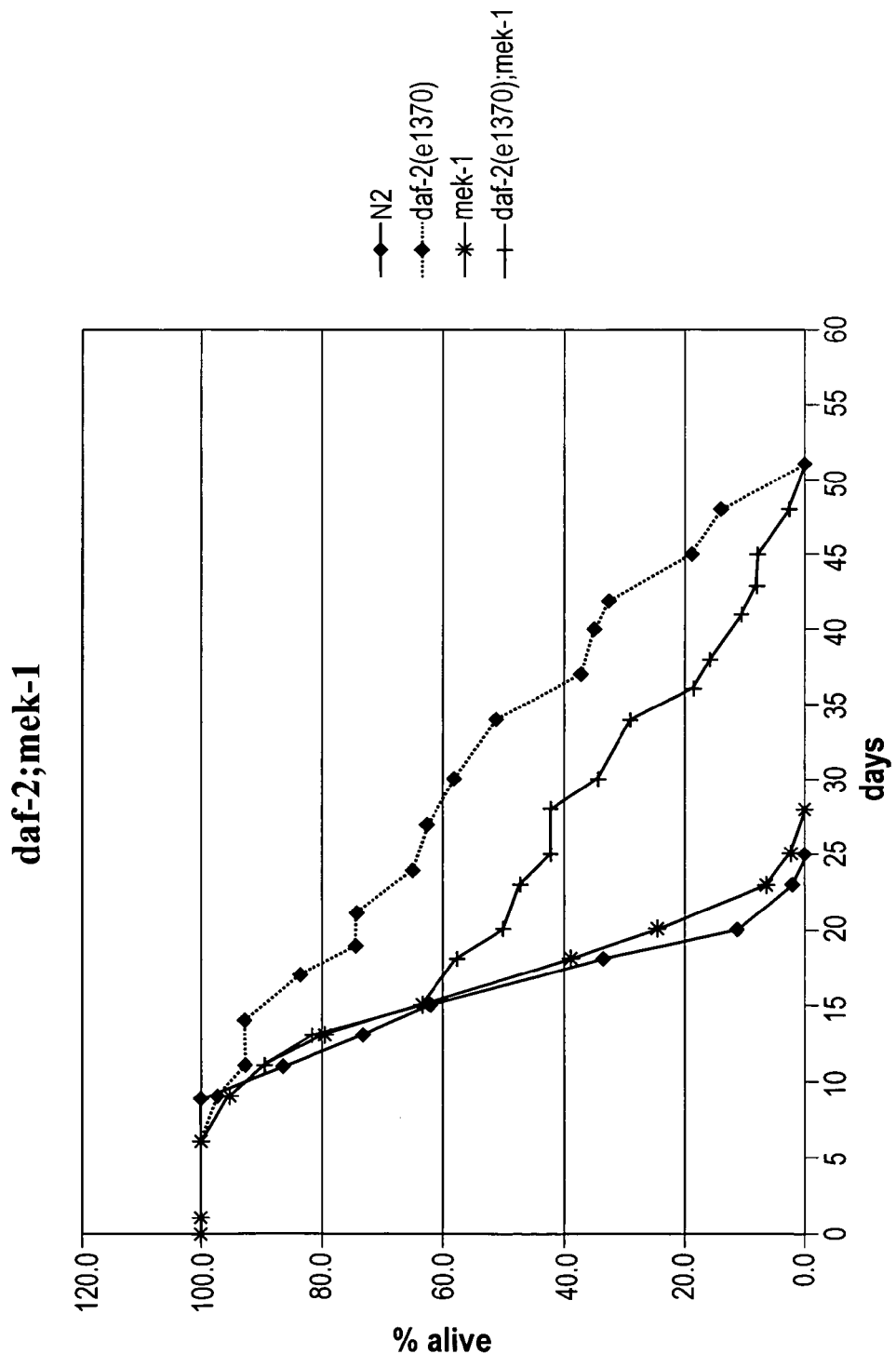

The term "insulin signaling pathway" (or "insulin-like signaling pathway") refers to the signaling pathway involving proteins (e.g., enzymes) and other non-protein molecules (e.g., precursors, substrates, intermediates or products), utilized in transmission of an intracellular signal from a cell membrane to the nucleus, in particular, from an insulin receptor (IR) or insulin-like growth factor (IGF) receptor at the cell surface to the nucleus. Additional signaling molecules in the insulin signaling pathway in mammals, for example, include insulin receptor substrate (IRS), phosphatidylinositol 3-kinase (PI3-K), PTEN phosphatase, phosphoinositide kinase 1 (PDK1), protein kinase B (PKB) and forkhead transcription factors (FKHR). Such signaling molecules in *C. elegans*, for example, include IST-1, DAF-2, AAP-1, AGE-1, PDK-1, AKT-1, DAF-18 and DAF-16 (and the corresponding genes encoding these molecules, i.e., ist-1, daf-2, aap-1, age-1, pdk-1, akt-1, akt-2, daf-18, and daf-16, respectively. FIG. 2 includes a schematic representation of the insulin signaling pathway.

The term "deregulated" or "deregulation" includes the alteration or modification of at least one molecule in a signaling pathway, such that signal transmission by the pathway is altered or modified. Preferably, the activity or expression of at least one enzyme in the pathway is altered or modified such that signal transmission by the pathway is altered or modified.

The term "upmodulated" refers to an increase or enhancement of the activity or expression of a signaling pathway molecule. The term "downmodulated" refers to a decrease or inhibition of the activity or expression of a signaling pathway molecule.

"Impaired JNK signaling" refers to genetic or other alterations that lead to reduced activity in the JNK signaling pathway in mammals, organisms, cells, etc. These alterations include, but are not limited to, inhibition of expression or activity of signaling molecules involved in insulin signaling in mammals, organisms, cells, etc.

"Impaired insulin signaling" refers to genetic or other alterations that lead to reduced activity in the insulin or insulin-like signaling pathway in mammals, organisms, cells, etc. These alterations include, but are not limited to, inhibition of expression or activity of signaling molecules involved in insulin signaling in mammals, organisms, cells, etc.

"Increased activity" or "enhanced activity" of a signaling molecule, for example, DAF-16 or a DAF-16 orthologue, refers to increased daf-16 or daf-16 orthologue transcription or translation, increased DAF-16 or DAF-16 orthologue activation and/or increased target protein activation.

A "target protein" of DAF-16 or a DAF-16 orthologue refers to any protein that DAF-16 or a DAF-16 orthologue either binds to directly in order to modulate, or whose transcription or translation is modulated by binding of DAF-16 or a DAF-16 homolog to the regulatory region of the gene or the mRNA encoding the protein. Target proteins can include, but are not limited to, HSP70, HSP90, catalase, ubiquitin and/or superoxide dismutase.

"Candidate agents" or "candidate molecules" means agents or molecules that can be tested in screening assays for suitability as agents to extend life span. Typically, candidate agents are small molecules, peptides, oligonucleotides and/or derivatives thereof, or other compounds known to be useful as screening candidates in the drug discovery field.

As used herein, the term "agent" means a biological or chemical compound such as a simple or complex organic or inorganic molecule, a peptide, protein, oligonucleotide, polynucleotide, carbohydrate, or lipoprotein. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. Compounds can be tested singly or in combination with one another.

As used herein, "expression" refers to the process by which polynucleotides are transcribed into mRNA and translated into peptides, polypeptides, or proteins.

An agent that "modulates" life-extension is an agent that affects life-extension, or lifespan, whether directly or indirectly, whether negatively or positively.

Various aspects of the invention are described in further detail in the following subsections.

I. Signaling Pathways

In mammalian insulin signaling, many signaling pathways operate downstream of the insulin receptor. One such pathway, the mitogen-activated protein kinase (MAPK) signaling pathway, is involved in regulating normal development, mitogenesis, and various stress responses (Kido Y. et al. (2001) *J of Clin Endocrin and Met* 86:972-979). MAPKs can be divided into three groups: the c-Jun N-terminal (JNK or stress-activated protein kinase); the extracellular signal-regulated kinase (ERK); and p38 kinases. MAPKs are activated via dual phosphorylation of threonine and tyrosine residues in their activation loops. The specific MAPK kinases (MAPKKs or MEKs) that carry out this reaction are themselves phosphorylated and activated by specific MAPKK kinases (MAPKKKs).

In the JNK signaling cascade (reviewed in Ip Y. T. & Davis R. J. (1998) *Curr Opin Cell Biol* 10:205-219; Weston C. R. & Davis R. J. (2002)12:14-21), JNK activity is strongly stimulated in vertebrate cell culture by inhibitors of protein biosynthesis, such as cycloheximide and anisomycin, by inflammatory cytokines, such as tumor necrosis factor-alpha (TNF-alpha) and interleukin-1B (IL-1B), and by heat, osmotic shock, UV light or other DNA-damaging agents. When JNK is activated, it migrates from the cytoplasmic compartment into the nucleus and stimulates the activity of several transcription factors including c-Jun, ATF-2, ELK-1 and p53. In mammalian cells, the JNK signal cascade begins with the stress-induced activation of MEKK4. MEKK4 in turn activates the two MAPKKs, MKK4 and MKK7, both of which are believed to activate JNK. While MKK4 also functions as an activator of p38, MKK7 probably functions as a specific activator of JNK (Cavigelli et al. (1995) *EMBO J.* 14:5957-5964; Derijard et al. (1995) *Science* 267:682-685; Tournier et al. (1997) *PNAS USA* 94:7337-7342). Finally, JNK in turn activates c-Jun.

In *C. elegans*, jnk-1 is the jnk homolog, mek-1 is highly homologous to mammalian mkk7, and jkk-1 has 41.6% identity with MKK7 in the kinase domain (Kawasaki et al. (1999) *EMBO J.* 18:3604-3615; Koga et al. (2000) *EMBO J.* 19:5148-5156). Both jnk-1 and jkk-1 are co-expressed in the cell bodies and the axons of most neurons (Kawasaki et al. (1999) *EMBO J.* 18:3604-3615), while mek-1 is expressed in pharyngeal muscles, uterus, a portion of intestine and neurons in the ring, ventral and anal ganglia (Koga et al. (2000) *EMBO J.* 19:5148-5156). Although individual jnk-1, jkk-1 or mek-1 mutants do not show developmental defects, disruption of jkk-1 or jnk-1 results in defective body movement coordination via type-D GABAergic motor neurons. In addition, disruption of jnk-1 or mek-1 results in hypersensitivity to heavy metals, such as copper and cadmium ions (Koga et al. (2000) *EMBO J.* 19:5148-5156; Kawasaki et al. (1999) *EMBO J.* 18:3604-3615; Villanueva, A. et al. (2001) *EMBO J.* 20:5114-5128).

The *C. elegans* genome also contains mkk-4, which is highly homologous to mammalian mkk-4. Inactivation of mkk-4 only resulted in an egg-laying defect in adult hermaphrodites, and thus this mutant did not display a similar phenotype to that of the other JNK pathway members (Villanueva A. et al. (2001) *EMBO J.* 20:5114-5128). Finally, the most recent member of the JNK signaling pathway to be identified in *C. elegans* is the gene unc-16. The gene unc-16 encodes a JIF scaffold protein homolog (Byrd D. T. et al. (2001) *Neuron* 32:787-800). The function of JIF proteins is to act to gather several of the components of the JNK pathway, including MKK7 and JNK, and in this way eases signal transmission by the signaling pathway (Yasuda J. et al. (1999) *Mol and Cell Biol* 19:7245-7254).

Prior to the instant invention, there was no knowledge of a role for the JNK signaling pathway in longevity. The instant inventors first performed life span analysis in various *C. elegans* strains having mutations in various JNK signaling pathway molecules. The JNK family was chosen as a potential pathway that could act downstream of daf-2 in insulin-like signaling (see background) for the following reasons:

(1) The JNK pathway is activated by the stress response, and daf-2 and age-1 mutants are known to be resistant to stresses, such as heat, oxidative damage and heavy metals (Lithgow G. J. et al. (1994) *J. Gerontol.* 49: B270-276; Lithgow, G. J., et al. (1995) *PNAS USA* 92:7540-4; Murakami S. & Johnson T. E. (1996) *Genetics* 143: 1207-1218; Honda Y. & Honda S. (1999) *FASED J* 13:1385-1393; Baryste D. et al. (2001) *FasEB J* 15:627-634; Friedman D. B. & Johnson T. E. (1988) *Genetics* 118:75-86; Gems D. et al. (1998) *Genetics* 150:129-155).

(2) Several genes in the JNK signaling pathway, including jnk-1 and the two MKK4 homologs, jkk-1 and mek-1, have already been isolated in *C. elegans*. These genes have been shown to affect resistance to stress; reducing the activity of any of these three genes yielded worms that displayed defective body movement coordination and/or hypersensitivity to heavy metal stresses (Villanueva A. et al. (2001) *EMBO J* 20:5114-5128; Koga M. et al. (2000) *EMBO J* 19:5148-5156; Kawasaki M. et al. (1999) *EMBO J* 18:3604-3615). This is relevant because both daf-2 and age-1 mutants are resistant to heavy metals and many other types of stress (reviewed in Kimura K. et al. (1997) *Science* 277:942-946). A strong correlation has been made between life span extension and stress resistance (Lithgow G. J. and Walker G. A. (2002) *Mech of Aging and Dev.* 123:765-771). A very recent publication has shown that heterozygous knockout mice for IGF-1R have extended life span and increased resistance to oxidative stress (Holzenberger M. et al. (2002) Nature, in press.), indicating that IGF-1R may be a central regulator of lifespan in mammals. While only one insulin-like receptor homolog, DAF-2, has been clearly identified in *C. elegans*, a very recent publication has reported a new family of putative insulin receptor-like proteins (Dlakic M., (2002) *Curr. Biol* 12(5) R155-R157). The correlation between life span extension and stress resistance suggests that the JNK signaling genes could play a role in life span regulation.

(3) In mammals, JNK interacts with the insulin receptor substrate (IRS) molecule and phosphorylates IRS at Ser307 in vitro and in vivo in mice (Aguirre V. et al. (2000) *J Biol Chem* 275: 9047-9054; J. Hirosumi et al. (2002) *Nature* 420:333-336). IRS is an adaptor molecule through which insulin receptor signals, both in mammalian systems and *Drosophila*. In obese mammals, TNF-alpha or FFA produced in adipose tissue activates JNK. Activated JNK in turn phosphorylates IRS at Ser307, causing an inhibition of IRS activity and thereby inhibiting insulin signaling. In this way, JNK promotes the development of insulin resistance that is associated with obesity and type 2 diabetes (J. Hirosumi et al. (2002) *Nature* 420:333-336). Very recent publications have identified the *C. elegans* homolog of IRS, named IST-1, along with AAP-1, the *C. elegans* homolog of the p50/p55 subunits of P13-K (Wokow C. A. et. al. (2002) *J. Biol. Chem.* 277:49591-49597).

Based on a detailed life span analysis in the various *C. elegans* mutants, it was discovered that reduction of function mutations in the JNK pathway cause either a reduction of life span or no change in life span in wild type background. The mutations were then placed in combination with a reduction of function mutation in the insulin-like receptor gene daf-2 or the downstream PI-3-kinase age-1. The resulting double mutant causes either a synergy in the life span (greater than either mutant alone) or a reduction of life span (intermediate: lower than the daf-2 or age-1 mutation alone but not quite down to the level of the JNK mutation on its own). Remarkably, even mutations that did not effect life span on their own, show an effect when placed in combination with another mutation that causes a change in levels of the insulin pathway (and therefore daf-16).

Based on these findings, novel screening assays have been developed for the identification of longevity-promoting agents (e.g., anti-aging agents), as well as therapeutic methods for increasing longevity and/or quality of life in aging individuals which feature targeting the JNK signaling pathway in such individuals. These features of the instant invention are described in detail in the following subsections.

II. Screening Assays

The methods of the invention are suitable for use in methods to identify and/or characterize potential pharmacological agents, e.g. identifying new pharmacological agents from a collection of test substances, in particular, pharmacological agents for use in increasing life span and/or enhancing quality of life in aged individuals. Pharmacological agents identified according to the methodologies of the invention are also useful, for example, in enhancing stress resistance in individuals, and increasing the cytoprotective abilities of cells.

The methods described herein are in vitro and in vivo cell- and animal (e.g., nematode)-based screening assays.

A. Screening in Whole Organisms

The invention provides screening assays in whole organisms. In the whole organism-based embodiments, whole organisms comprising the organism having a deregulated JNK signaling pathway and/or insulin signaling pathway are used for testing agents. In a particular embodiment, the deregulated JNK signaling pathway is downmodulated. In another embodiment, the deregulated JNK signaling pathway is upmodulated.

The invention provides a method for identifying an agent capable of enhancing longevity, comprising: (a) contacting an organism having a deregulated c-jun N-terminal kinse (JNK) signaling pathway with a test agent, wherein a detectable phenotype is associated with the deregulated JNK signaling pathway; and (b) assaying for the ability of the test agent to effect said phenotype, wherein the agent is identified based on its ability to alter said phenotype as compared to a suitable control. A variation on this method comprises (a) contacting an organism further having a deregulated insulin signaling pathway, wherein said detectable phenotype is associated with said deregulated JNK signaling pathway and said deregulated insulin signaling pathway, and (b) assaying for the ability of the test agent to effect said phenotype, wherein the agent is identified based on its ability to alter said phenotype as compared to a suitable control.

In one embodiment, the deregulated insulin signaling pathway molecule is selected from the group consisting of DAF-2, IST-1, AAP-1, AGE-1, PDK-1, AKT-1, AKT-2 and DAF-18, or a mammalian orthologue thereof. In another embodiment, the deregulated JNK signaling pathway molecule is selected from the group consisting of (UNC-16), (MEK-1), (JKK-1), and c-jun N-terminal kinse-1 (JNK-1), or a mammalian orthologue thereof.

In a preferred embodiment of the invention, the roundworm *Caenorhabditis elegans* is employed. *C. elegans* is a simple soil nematode species that has been extensively described at the cellular and molecular level, and is a model organism for biological studies. *C. elegans* can develop through a normal life cycle that involves four larval stages and a final molt into an adult hermaphrodite. The dauer pathway is an alternative life cycle stage common to many nematode species which is normally triggered by environmental stresses such as starvation, temperature extremes, or overcrowding. Genetically, the dauer pathway has been most intensively studied in *C. elegans*. The response to overcrowding in *C. elegans* is mediated by a substance known as dauer pheromone, which is secreted by the animals. When dauer pheromone becomes sufficiently concentrated, it triggers commitment to the dauer alternative life cycle stage. A strong correlation exists between a constitutive dauer and the long-lived phenotype.

In preferred embodiments of the invention, the detectable phenotype is increased or decreased life span. In another embodiment, the detectable phenotype is constitutive dauer formation or defective dauer formation. In other embodiments, the phenotype is increased or decreased body size, or increased or decreased stress resistance, wherein stress resistance is selected from, but not limited to, the group consisting of oxidative stress, ultraviolet (UV) stress, hypoxic stress, heavy metal stress and heat stress.

When screening for an effect of dauer formation, the assay population of *C. elegans* is preferably exposed to test agent during the portion of the life cycle at which commitment to the dauer pathway is made. Measurement of dauer formation has been previously described. See e.g., Riddle et al., Genetic and Environmental Regulation of Dauer Larva Development, In Riddle, Blumenthal, Meyer, and Priess (eds), *C. ELEGANS* II., Cold Spring Harbor Laboratory Press, Cold Spring Harbor, N.Y. (1997). In mutant strains containing deregulated JNK and/or insulin signaling and exhibiting a constitutive dauer phenotype, an agent is identified based on its ability to reverse that phenotype.

Life span assays have also been well described (Apfeld J. & Kenyon C. (1998) *Cell* 95: 199-210). In strains that exhibit an extended life span phenotype, an agent is identified based on its ability to either further extend or shorten the lifespan. Resistance to ultraviolet (UV) stress is determined by exposing the organism to UV light and measuring life span from the day of UV treatment. Oxidative stress resistance is determined by exposing the animals to paraquat, which produces superoxide when taken up by cells, and determining survival from the day of treatment (Feng et al. (2001) Dev. Cell 1:1-20.). Heat tolerance is measured by exposing adult animals to a 35° C. heat shock for 24 hours, and then scoring the animals for viability.

In assay formats featuring indicator phenotypes, the phenotype of the animals may be detected by direct observation. An alternative to direct observation is mechanical detection of the animals. For instance, such detection could involve the determination of optical density across the test surface by a machine. The animals would be detected by changes in density at the location where an animal was located. Alternatively, if the animals are expressing a reporter gene that can be detected in living animals (e.g., GFP), a machine could monitor the animals using a suitable reporter gene detection protocol.

If desired, additional tests may be conducted using the agent identified to further characterize the nature of the agent's function with respect to longevity. For example, egg laying may also be measured to determine whether the longevity occurs by delaying maturity. As another example, other phenotypes associated with other gerontogenes could be tested to determine whether the identified agent affects functional pathways associated with these other genes.

Another embodiment of the invention provides a method for identifying an agent capable of enhancing longevity, comprising: (a) contacting an organism having a c-jun N-terminal kinse (JNK) signaling pathway with a test agent; (b) assaying for the ability of the test agent to effect a downstream indicator of said c-jun N-terminal kinse (JNK) signaling pathway, wherein the agent is identified based on its ability to alter said indicator as compared to a suitable control. In one embodiment, the JNK signaling pathway is deregulated.

In such assays, the organism is a nematode. In a preferred embodiment, the nematode is *C. elegans*. In a further embodiment, the organism is a parasitic nematode. In one embodiment, the organism is not an insect. In yet another embodiment, the deregulated signaling molecule in said assay is selected from the group consisting of (UNC-16), (MEK-1), (JKK-1), and c-jun N-terminal kinse-1 (JNK-1).

In another embodiment, the indicator is selected from, but not limited to, the group consisting of DAF-16, superoxide dismutase (SOD), glucose transporter 4 (GLUT4) and glucose transporter 1 (GLUT1). Recent publications indicate that two other members of the insulin-like signaling pathway in *C. elegans*, DAF-9 and DAF-12, function downstream of DAF-16 (Gerisch B. et al. (2001) *Dev. Cell*, 1(6):841-51; Jia K. et al. (2002) *Development* 129:221-231). In *C. elegans*, daf-9 encodes a cytochrome P450 related to vertebrate steroidogenic hydroxylases, suggesting it could metabolize a DAF-12 ligand. In another embodiment, therefore, the indicator may be either DAF-9 or DAF-12.

In such an assay, the agent may be identified based on its ability to increase or decrease the indicator. The agent may alter expression of the indicator, wherein the expression is nucleic acid expression or polypeptide expression. The alteration of expression may be a change in the rate of expression or steady state expression.

In one embodiment, the agent alters the activity of the indicator. In a preferred embodiment, the agent may alter the post-translational modification state of the indicator, e.g. the phosphorylation state of the indicator. Techniques are well known in the art for analyzing phosphorylation and other post-translational modification states. For example, phosphorylation may be determined by the use of antibodies to phospho-epitopes to detect a phosphorylated polypeptide by Western analysis.

In another embodiment, the agent may alter the cellular localization of the indicator, such as from cytoplasmic to nuclear. Changes in cellular localization can be determined by introducing a chimeric form of the indicator containing a reporter gene. Plasmid constructs can be introduced into *C. elegans* using described transformation methods. See e.g., Mello et al., (1991) *EMBO J.* 10:3959-3970. Preferably, the plasmid constructs are linear constructs. An important aspect of transformation in *C. elegans* is that plasmid constructs can be easily cotransformed, thus allowing for assay formats in which *C. elegans* are engineered to express, for example, non-*C. elegans* signaling pathway molecules and reporter genes. Preferably, a reporter gene is used that can be scored in a living animal, but does not affect the indicator phenotype of the animal. For example, green fluorescent protein (herein referred to as "GFP") is a widely used reporter molecule in living systems. Ellenberg (1999) *Trends Cell Biol.* 9:52-56; Chalfie et al., (1994) *Science* 263:802-805.

B. Cell-Based Screening Assays

The invention further features cell-based assays for the identification of an agent capable of enhancing longevity. In one embodiment, the invention provides methods for identifying an agent that enhances longevity, comprising (a) contacting a cell with a test agent, said cell having a JNK signaling pathway; (b) detecting an indicator of JNK signaling; and (c) identifying the agent based on its ability to modulate JNK signaling in said cell. The invention further provides a method for identifying an agent that enhances longevity, comprising (a) contacting a cell with a test agent, said cell having a JNK signaling pathway and an insulin signaling pathway; (b) detecting an indicator of JNK signaling and insulin signaling; and (c) identifying the agent based on its ability to modulate JNK signaling and insulin signaling in said cell.

The cell-based screening assays described herein have several advantages over conventional drug screening assays: 1) if an agent must enter a cell to achieve a desired therapeutic effect, a cell-based assay can give an indication as to whether the agent can enter a cell; 2) a cell-based screening assay can identify agents that, in the state in which they are added to the assay system are ineffective to modulate the JNK and/or insulin signaling polynucleotide and/or polypeptide function, but that are modified by cellular components once inside a cell in such a way that they become effective agents; 3) most importantly, a cell-based assay system allows identification of agents affecting any component of a pathway that ultimately results in characteristics that are associated with JNK and/or insulin signaling polynucleotide and/or polypeptide function.

In one embodiment, the agent is identified based on the ability to inhibit JNK signaling. In a preferred embodiment, the agent is identified based on the ability to inhibit JNK signaling and additionally to inhibit insulin signaling. In another preffered embodiment, the agent is identified based on the ability to enhance JNK signaling. In another embodiment, the agent is identified based on the ability to enhance JNK signaling and inhibit insuling signaling. In preferred embodiments, the indicator is altered cellular localization of DAF-16, e.g., nuclear localization of DAF-16.

In one embodiment, suitable host cells include, but are not limited to, fungi (including yeast), bacterial, insect and mammalian. In a preferred embodiments, the host cell is a human cell or is derived from a nematode. In one embodiment, the cell is not an insect cell.

An indicator of the JNK signaling and/or insulin signaling may include a JNK signaling and/or insulin signaling polynucleotide and/or polypeptide. Characteristics associated with said JNK signaling and/or insulin signaling polynucleotide and/or polypeptide depend upon the polynucleotide or polypeptide. Functional characteristics include, but are not limited to, transcription, translation (including levels of precursor and/or processed polypeptide), location of protein product (such as nuclear or membrane localization), post-translational modification of protein product (such as phosphorylation or acetylation), any enzymatic activities, such as kinase activity, structural and/or functional phenotypes (such as stress resistance or life cycle), and expression (including repression or de-repression) of any other genes known to be controlled (modulated) by the polynucleotide. Any measurable change in any of these and other parameters indicate that the agent may be useful. In a preferred embodiment, given that JNK and/or insulin signaling pathway molecules that regulate longevity have been identified by their ability to confer life extension when their function is reduced, useful agents will preferably be agents that confer decreased functionality. In another preferred embodiment, given that over-expression of JNK signaling pathway molecules, e.g., JNK, have been identified to confer life extension, useful agents will additionally preferably be agents that confer increased activity or expression, e.g., overexpression, of JNK signaling pathway molecules.

Modulation of function of a JNK signaling pathway molecule, polynucleotide and/or polypeptide, may occur at any level. An agent may modulate function by reducing or preventing transcription of a JNK signaling pathway polynucleotide. An example of such an agent is one that binds to the upstream controlling region, including a polynucleotide sequence or polypeptide. An agent may modulate translation of mRNA. An example of such an agent is one that binds to the mRNA, such as an anti-sense polynucleotide, or an agent which selectively degrades or stabilizes the mRNA. An agent may modulate function by binding to the JNK signaling pathway polypeptide. An example of such an agent is a polypeptide or a chelator.

In preferred embodiments, to identify agents that inhibit JNK and/or insulin signaling, the skilled artisan could look for conversion of a substrate to the corresponding product catalyzed by a downstream enzyme in the signaling pathway. The artisan could look for activation or inhibition of a downstream enzyme in the pathway, for example the activation of downstream kinase in the JNK signaling pathway. The artisan could further look for an alteration of a transcriptional event regulated by the pathway, such as the expression of a nuclear factor regulated by the pathway. Another indicator may be the activation or inhibition of a transcription factor regulated by the pathway. In each of these instances, the indication may involve an endogenous gene or protein. Alternatively, the indication could involve a reporter gene or protein.

Measuring all of these parameters (such as those using reporter genes) involve methods known in the art and need not be discussed herein. For example, degree of transcription can be measured using standard Northern analysis. Amount of expression product may be measured simply by Western analysis (if an antibody is available) or by a functional assay that detects the amount of protein, such as kinase activity.

Cell-based screening assays of the present invention can be designed, e.g., by constructing cell lines or strains of animals in which the expression of a reporter protein, i.e., an easily assayable protein, such as β-galactosidase, chloramphenicol acetyltransferase (CAT), green fluorescent protein (GFP) or hiciferase, is dependent on JNK and/or insulin signaling polynucleotide and/or polypeptide function. The cell is exposed to a test agent, and, after a time sufficient to effect β-galactosidase expression and sufficient to allow for depletion of previously expressed β-galactosidase, the cells are assayed for the production of β-galactosidase under standard assaying conditions.

Reporter genes include, but are not limited to, alkaline phosphatase, chloramphenicol acetyl transferase, galactosidase, luciferase and green fluorescent protein. Identification methods for the products of reporter genes include, but are not limited to, enzymatic assays and fluorimetric assays. Reporter genes and assays to detect their products are well known in the art and are described, for example in Current Protocols in Molecular Biology, eds. Ausubel et al., Greene Publishing and Wiley-Interscience: New York (1987) and periodic updates. Reporter genes, reporter gene assays and reagent kits are also readily available from commercial sources (Stratagene, Invitrogen and etc.).

Introduction of JNK and/or insulin signaling polynucleotides (or reporter gene polynucleotides) depend on the particular host cell used and may be by any of the many methods known in the art, such as microinjection, spheroplasting, electroporation, CaCl, precipitation, lithium acetate treatment, and lipofectamine treatment.

Polynucleotides introduced into a suitable host cell(s) are polynucleotide constructs comprising a JNK and/or insulin signaling polynucleotide. These constructs contain elements (i.e., functional sequences) which, upon introduction of the construct, allow expression (i.e., transcription, translation, and post-translational modifications, if any) of JNK and/or insulin signaling polypeptide amino acid sequence in the host cell. The composition of these elements will depend upon the host cell being used. For introduction into *C. elegans*, polynucleotide constructs will generally contain the JNK and/or insulin signaling polynucleotide operatively linked to a suitable promoter and will additionally contain a selectable marker such as rol-6 (sul 006). Other suitable host cells and/or whole animals include, for example, insect, yeast and mammalian cells. In one embodiment, the host cells and/or whole animals are not insects, e.g., *Drosophila*. Suitable selectable markers for nematode cells are those that enable the identification of cells that have taken up the nucleic acid, such as morphologic and behavioral markers such as rol-6 or visual markers such as green fluorescent protein. Screening of the transfectants identifies cells or animals that have taken up and express the polynucleotide.

In some embodiments, a JNK and/or insulin signaling polynucleotide is operatively linked to an inducible promoter. Use of an inducible promoter provides a means to determine whether the agent is acting via a pathway involving the JNK and/or insulin signaling polynucleotide. If an agent modulates a functional characteristic of a JNK and/or insulin signaling polynucleotide and/or polypeptide in a cell in which the inducible promoter is activated, an observation that the agent fails to elicit the same result in a cell in which the inducible promoter is not activated indicates that the agent is affecting at least one step or aspect of JNK and/or insulin signaling polynucleotide function. Conversely, if the functional characteristic is also observed in a cell in which the inducible promoter is not activated, then it can be assumed that the agent is not necessarily acting solely via the JNK and/or insulin signaling polynucleotide functional pathway.

C. In Vitro Screening Assays

In the in vitro embodiments, an agent is tested for its ability to modulate activity or expression of a JNK signaling pathway and, optionally, additionally an insulin signaling pathway molecule using the methods described herein.

The invention provides an in vitro method of identifying an agent capable of enhancing longevity, comprising (a) contacting an assay composition with a test compound, wherein the assay composition comprises a JNK signaling pathway molecule; (b) detecting activity or expression of the JNK signaling pathway molecule, wherein the agent is identified based on its ability to modulate activity or expression of the JNK signaling pathway molecule.

The invention further provides an in vitro method of identifying an agent capable of enhancing longevity, comprising (a) contacting a first assay composition with a test compound, wherein the assay composition comprises a JNK signaling pathway molecule; (b) detecting activity or expression of the JNK signaling pathway molecule; (c) contacting a second assay composition with the test compound, wherein the assay composition comprises an insulin signaling pathway molecule; and (d) detecting activity or expression of the insulin signaling pathway molecule, wherein the agent is identified based on its ability to modulate activity or expression of the JNK signaling pathway molecule and insulin signaling pathway molecule.

In one embodiment, the JNK signaling pathway molecule may be selected from the group consisting of UNC-16, MEK-1, JKK-1, and c-jun N-terminal kinse-1 (JNK-1), or a mammalian orthologue thereof. In another embodiment, the insulin signaling pathway molecule may be selected from the group consisting of DAF-2, IST-1, AAP-1, AGE-1, PDK-1, AKT-1, AKT-2 and DAF-18, or a mammalian orthologue thereof.

In such an assay, the JNK signaling molecule and insuling signaling molecule may be polynucleotide(s) or polypeptide(s). In such an assay, the JNK signaling molecule and insuring signaling molecule may be present as part of a cell-free extract or a partially purified system. Alternatively, they may be purified or recombinant. The signaling pathway molecules to be used in these screening methods may be obtained using standard synthetic methods known in the art, including, but not limited to, isolation from natural sources, recombinant methods, chemical synthetic methods, and enzymatic digestion followed by purification.

The modulation of activity or expression of the JNK and insulin signaling molecules may be an increase or a decrease. In such an assay, the detection of the activity or expression of the insulin signaling and JNK signaling molecules can be studied using standard techniques. In a preferred embodiment, the agent is identified based on its ability to increase the activity or expression of the JNK signaling molecule. In another preferred embodiment, the agent is identified based on its ability to decrease the activity or expression of the insulin signaling molecule and the JNK signaling molecule. In yet another embodiment, the agent is identified based on its ability to decrease the activity or expression of the insulin signaling molecule and to increase the activity or expression of the JNK signaling molecule.

In preferred embodiments, an agent is screened in an in vitro screening assays, which may be any of the following: (1) an assay that determines whether an agent is modulating transcription of a JNK signaling pathway and insulin signaling pathway polynucleotide; (2) an assay for an agent which modulates translation of mRNA or polynucleotides encoding a JNK signaling pathway molecule and an insuling signaling pathway molecule; (3) an assay for an agent that binds to a JNK signaling pathway and an insulin signaling pathway polynucleotide or polypeptide; (4) an assay for an agent that modulates post-translational modification of a JNK or insulin signaling polypeptide.

For an assay that determines whether an agent modulates transcription of a JNK or insulin signaling polynucleotide, an in vitro transcription or transcription/translation system may be used. These systems are available commercially, and generally contain a coding sequence as a positive, preferably internal, control. A JNK and/or insulin signaling polynucleotide is introduced and transcription is allowed to occur. Comparison to transcription products between an in vitro expression system that does not contain any agent (negative control) with an in vitro expression system that does contain the agent indicates whether an agent is affecting transcription. Comparison of transcription products between control and the JNK or insulin signaling polynucleotide indicates whether the agent, if acting on this level, is selectively affecting transcription of the JNK or insulin signaling polynucleotide (as opposed to affecting transcription in a general, non-selective or specific fashion).

For an assay that determines whether an agent modulates translation of a JNK or insulin signaling mRNA or a polynucleotide encoding a JNK or insulin signaling polypeptide, an in vitro transcription/translation assay as described above may be used, except the translation products are compared. Comparison of translation products between an in vitro expression system that does not contain any agent (negative control) with an in vitro expression system that does contain agent indicates whether an agent is affecting transcription. Comparison of translation products between control and the JNK or insuling signaling polynucleotide indicates whether the agent, if acting on this level, is selectively affecting translation of the JNK or insulin signaling polynucleotide (as opposed to affecting translation in a general, nonselective or unspecific fashion).

For an assay for an agent that binds to a JNK or insulin signaling polypeptide, a JNK or insulin signaling polynucleotide is first recombinantly expressed in a prokaryotic or eukaryotic expression system as a native or as a fusion protein in which a JNK or insulin signaling polypeptide (or fragment thereof) is conjugated with a well-characterized epitope or protein as are well known in the art. Recombinant JNK and/or insulin signaling polypeptide is then purified by, for instance, immunoprecipitation using anti-JNK and/or insulin signaling polypeptide antibodies or anti-epitope antibodies or by binding to immobilized ligand of the conjugate. An affinity column made of JNK and/or insulin signaling polypeptide or JNK and/or insulin signaling polypeptide fusion protein is then used to screen a mixture of compounds which have been appropriately labeled. Suitable labels include, but are not limited to flurochromes, radioisotopes, enzymes and chemiluminescent compounds. The unbound and bound compounds can be separated by washes using various conditions (e.g. high salt, detergent) that are routinely employed by those skilled in the art. Non-specific binding to the affinity column can be minimized by pre-clearing the compound mixture using an affinity column containing merely the conjugate or the epitope. A similar method can be used for screening for agents that competes for binding to a JNK and/or insulin signaling polypeptide. In addition to affinity chromatography, there are other techniques such as measuring the change of melting temperature or the fluorescence anisotropy of a protein which will change upon binding another molecule. For example, a BIAcore assay using a sensor chip (supplied by Pharmacia Biosensor, Stitt et al. (1995) Cell 80: 661-670) that is covalently coupled to native JNK or insulin signaling polypeptide or JNK or insulin signaling polypeptide fusion proteins, may be performed to determine the JNK or insulin signaling polypeptide binding activity of different agents.

In another embodiment, an in vitro screening assay detects agents that compete with another substance (most likely a polypeptide) that binds a JNK or insulin signaling polypeptide. Competitive binding assays are known in the art and need not be described in detail herein. Briefly, such an assay entails measuring the amount of JNK or insulin signaling polypeptide complex formed in the presence of increasing amounts of the putative competitor. For these assays, one of the reactants is labeled using, for example, $^{32}$P.

In another embodiment, an in vitro screening assay detects agents that modulate the post-translational modification of a polypeptide. For example, techniques can be used for studying phosphorylation of proteins (such as DAF-16) or acetylation of proteins by using antibodies to phospho-epitopes or acetyl group-epitopes.

It is also understood that the in vitro screening methods of this invention include structural, or rational, drug design, in which the amino acid sequence, three-dimensional atomic structure or other property (or properties) of a JNK or insulin signaling polynucleotide or polypeptide provides a basis for designing an agent which is expected to bind to a JNK or insulin signaling polynucleotide or polypeptide. Generally, the design and/or choice of agents in this context is governed by several parameters, such as the perceived function of the polynucleotide or polypeptide target, its three-dimensional structure (if known or surmised), and other aspects of rational drug design. Techniques of combinatorial chemistry can also be used to generate numerous permutations of candidate agents. For purposes of this invention, an agent designed and/or obtained by rational drug designed may also be tested in the cell-based assays described above.

D. Test Compounds

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.)).

In a preferred embodiment, the library is a natural product library, e.g., a library produced by a bacterial, fungal, or yeast culture. In another preferred embodiment, the library is a synthetic compound library.

E. Suitable Controls

Assay methods generally require comparison to a control sample to which no agent is added. The screening methods described above represent primary screens, designed to detect any agent that may exhibit anti-aging activity. The skilled artisan will recognize that secondary tests will likely be necessary in order to evaluate an agent further. For example, a cytotoxicity assay would be performed as a further corroboration that an agent which tested positive in a primary screen would be suitable for use in living organisms. Any assay for cytotoxicity would be suitable for this purpose, including, for example the MTT assay (Promega).

This invention further pertains to novel agents identified by the above-described screening assays. Accordingly, it is within the scope of this invention to further use an agent identified as described herein in an appropriate animal model, e.g., an animal model to determine the efficacy, toxicity, or side effects of treatment with such an agent.

III. Recombinant Cells and Organisms

The methodologies of the present invention feature cells and organisms, e.g., recombinant cells and organisms, preferably including vectors or genes (e.g., wild-type and/or mutated genes) as described herein and/or cultured in a manner which results in the overexpression of a JNK signaling pathway molecule, e.g., JNK, JKK-1, UNC-16, or MEK-1. The term "recombinant" cell or organism includes a cell (e.g., mammalian cell or nematode cell) or organism (e.g., nematode, e.g., C. elegans) which has been genetically altered, modified or engineered (e.g., genetically engineered) such that it exhibits an altered, modified or different genotype and/or phenotype (e.g., when the genetic modification affects coding nucleic acid sequences of the cell or organism) as compared to the naturally-occurring cell or organism from which it was derived. Preferably, a "recombinant" cell or organism of the present invention has been genetically engineered such that it overexpresses at least one gene or gene product (e.g., a JNK signaling pathway gene or gene product) as described herein. The ordinary skilled will appreciate that a cell or organism expressing or overexpressing a gene product produces or overproduces the gene product as a result of expression or overexpression of nucleic acid sequences and/or genes encoding the gene product.

Suitable host cells and/or whole animals include, but are not limited to, for example, nematode (e.g., C. elegans), insect, yeast and mammalian cells. In one embodiment, the host cells and/or whole animals are not insects, e.g., Drosophila.

The term "overexpressed" or "overexpression" includes expression of a gene product (e.g., a JNK signaling pathway molecule, e.g., JNK, JKK-1, UNC-16, or MEK-1) at a level greater than that expressed prior to manipulation of the cell or organism or in a comparable cell or organism which has not been manipulated. In particular embodiments of the invention, overexpression is at least about 2, 3, 4, 5, 6, 7, 8, 9, 10, 11, 12, 13, 14, 15, 16, 17, 18, 19, 20, 25, 30, 40, 50 or more fold overexpression as compared to that expressed prior to manipulation of the cell or organism or in a comparable cell or organism which has not been manipulated.

In one embodiment, the cell or organism can be genetically manipulated (e.g., genetically engineered) to overexpress a level of gene product greater than that expressed prior to manipulation of the cell or organism or in a comparable cell or organism which has not been manipulated. Genetic manipulation can include, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a gene product, or any other conventional means of deregulating expression of a particular gene routine in the art (including but not limited to use of antisense nucleic acid molecules, for example, to block expression of repressor proteins).

In another embodiment, the cell or organism can be physically or environmentally manipulated to overexpress a level of gene product greater than that expressed prior to manipulation of the cell or organism or in a comparable cell or organism which has not been manipulated. For example, a cell or organism can be treated with or cultured in the presence of an agent known or suspected to increase transcription of a particular gene and/or translation of a particular gene product such that transcription and/or translation are enhanced or increased. Alternatively, a cell or organism can be cultured at a temperature selected to increase transcription of a particular gene and/or translation of a particular gene product such that transcription and/or translation are enhanced or increased.

The term "deregulated" or "deregulation" includes the alteration or modification of at least one gene in a cell or organism that is involved in a signaling pathway, e.g., the JNK signaling pathway or the insulin signaling pathway, such that the signal transmission by the pathway is altered or modified. Preferably, the activity or expression of at least one enzyme in the pathway is altered or modified such that signal transmission by the pathway is altered or modified. In a particular embodiment, the methodologies of the present invention feature recombinant cells or organisms in which the activity or expression of a JNK signaling pathway molecule, e.g., JNK, JKK-1, UNC-16, MEK-1 or a mammalian orthologue thereof, is increased. In a preferred embodiment, at least one gene that encodes a JNK signaling pathway molecule, e.g., JNK, is altered or modified such that the gene product is enhanced or increased. Other preferred "recombinant" cells or organisms of the present invention have a deregulated insulin signaling pathway. In particular embodiments, at least one gene that encodes an insulin signaling pathway molecule, e.g., DAF-2, AAP-1, IRS, AGE-1, PDK-1, AKT-1, AKT-2, or DAF-18 or a mammalian orthologue thereof, is altered or modified such that the gene product is enhanced or increased. For example, in one embodiment, a recombinant cell or organism is designed or engineered such that the activity or expression of a JNK signaling molecule, e.g., JNK, is increased and the activity or expression of at least one insulin signaling molecule is decreased, e.g., inhibited. In another embodiment, a recombinant cell or organism is designed or engineered such that the activity or expression of a JNK signaling molecule, e.g., JNK, is decreased and the activity or expression of at least one insulin signaling molecule is decreased, e.g., inhibited.

IV. Methods of Treatment

The present invention provides methods of treating a subject in need thereof with an agent which modulates JNK signaling, for example, an agent identified according to one of the above-described screening assays. "Treatment", or "treating" as used herein, is defined as the application or administration of a pharmacological agent of the invention to a subject, or application or administration of said agent to an isolated tissue or cell line from a subject, in particular an adult subject, an aging subject or an aged subject such that the desired outcome is achieved.

The present invention provides a method of enhancing longevity in a subject, involving selecting a subject in need of enhanced longevity, and administering to said subject a pharmacologically effective dose of an agent that modulates a JNK signaling pathway molecule, wherein modulation of said JNK signaling pathway molecule in said subject enhances longevity. In preferred embodiments, the agent increases the activity or expression of a JNK signaling pathway molecule, e.g., JNK, MKK4, MKK7, JIF scaffold protein, or MAP Kinase Kinase Kinases. Preferably, the agent increases the activity or expression of JNK. In a particular embodiment of the invention, the method of enhancing longevity in a subject further involves administering a pharmacologically effective dose of an agent that inhibits an insulin signaling pathway molecule, e.g., insulin receptor, insulin-like growth factor, insulin receptor substrate, phosphatidylinositol 3-kinase, PTEN phosphatase, phosphoinositide kinase 1, protein kinase B and forkhead transcription factors.

Such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

The modulators of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population).

The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

This invention is further illustrated by the following examples which should not be construed as limiting. The contents of all references, patents and published patent applications cited throughout this application are incorporated herein by reference.

EXAMPLES

Example 1

Combined Reduction of Function Mutations in a JNK Pathway Gene and daf-2 Leads to an Enhancement (jnk-1, unc-16, jkk-1) or Suppression (mek-1) of Life Span Extension Associated with daf-2 Mutant To identify other signaling pathways downstream of DAF-2, animals were generated having a reduction of function mutation in the DAF-2 receptor combined with a mutation in a kinase whose signaling pathway is implicated in mammalian insulin signaling. It was postulated that since mutations in daf-2 affect so many pathways, a novel interaction could be identified by looking at a subset of the phenotypes displayed in these double mutants. Such genes might not yet have been found because they only affect a subset of the daf-2 mutant phenotypes. Alternatively, such double mutants in combination with daf-2 could be dead. It has been suggested that the complete loss of function mutation in daf-2 is lethal (Gems D. et al. (1998) *Genetics* 150: 129-155), and a knock-out of the insulin receptor in mice creates pups that survive only a few weeks (Sone H. et al. (2001) *Trends in Mol Med* 7:320-322).

This approach was applied to the JNK signaling pathway. First, a panel of *C. elegans* mutants were produced. *C. elegans* strains were obtained containing a reduction-of-function mutation in jkk-1, mek-1, jnk-1 or unc-16. *C. elegans* strains were also constructed containing a loss or reduction-of-function mutation in jkk-1, mek-1, jnk-1 or unc-16 in combination with a reduction-of-function mutation in daf-2 or age-1. The phenotypes of these mutants were assessed using a standard assay for life span in order to test whether these JNK pathway genes modulated the life span extension associated with a single daf-2 or age-1 mutant.

Strains and Media

Strains included: N2 (wild type), jnk-1 (gk7), jkk-1 (km-2), mek-1 (ks54), unc-16 (e109), age-1 (hx546), daf-2 (e1370), daf-16 (mu86). Strains were obtained from the Center of *Caenorhabditis elegans* Genetics Center (University of Minnesota, Minneapolis, Minn.). Nematodes were cultured under standard conditions (Brenner S. (1974) *Genetics* 77:71-94).

Strain Construction

To construct double mutant strains, the following general approach was used: daf-2, age-1, or daf-16 males were obtained by heat-shock at 30° C. for 6 hours, and these males were used to mate with jnk-1, jkk-1, mek-1, or unc-16 hermaphrodites. For example, daf-2 (e1370) males were mated to jnk-1 hermaphrodites at 15 or 20° C., and 5-7 (15) or 3-4 (20) days later, putative cross progeny were singled to individual plates at 25° C. and allowed to have progeny. Three days later, the plates were scored for the presence of dauers (daf-2). Plates that segrated dauers were kept. Dauers were then returned to 15° C. to recover and singled to individual plates. These recovered dauers were allowed to have progeny and then were tested for presence or absence of the jnk-1 mutation by PCR. Matings were done typically at 15° C. and 20° C. depending on the strain.

Strain Characterization

The identity of all single and double mutants were confirmed by PCR as well as by phenotypic and complementation analysis. Homozygote F2 worms were identified by dauer formation at 25° C. (daf-2) or 27° C. (age-1), phenotype (unc-16 and mek-1), and PCR amplification (ink-1, jkk-1, and daf-16). The condition for PCR was 34 cycles of 94° C. for 30 sec, 50° C. for 1 min, and 72° C. for 3 min, followed by 72° C. extension for 10 min. Primers used for PCR were jnk-1 (5'-ACAGTGGAACAGGAGGAGGA-3' (SEQ ID NO:1) and 5'-ATGCCTATCTGCCTGAGAGC-3' (SEQ ID NO:2), jkk-1 (5'-AGGAGAAAAGCAAGTTGTCG-3' (SEQ ID NO:3) and 5'-GCAGCAGCTTTCACAACAC-3' (SEQ ID NO:4), and daf-16 (5'CAATGAGCAATGTGGACAGC-3' (SEQ ID NO:5) and 5'-CCGTCTGGTCGTTGTCTTTT-3' (SEQ ID NO:6)).

Life Span Assay

Life span assays were performed as described (Apfeld & Kenyon (1998) *Cell* 95:199-210). Briefly, life span was determined on seeded NGM (nematode growth media) plates at 20° C. Adult hermaphrodites were picked (4-10 per plate) from each strain and allowed to undergo one full generation at 15° C. or 20° C. From these plates, individual L4s or young adults were picked to plates at 20° C. containing 400 µg/ml FUDR. FUDR blocks DNA synthesis and causes animals to lay eggs that do not develop, thereby eliminating the need to transfer animals throughout the life span assay. Survival of the hermaphrodites was measured every few days by tapping. Animals were considered dead if no pharyngeal pumping was evident and they failed to respond to repeated prodding (Johnson T. et al. (1982) *PNAS* 79:6603-7).

Single Mutant Phenotypes

Several single mutants in the JNK pathway were already known to be stress sensitive. Many studies have shown a correlation between stress resistance and extended life span. The life span of single reduction of function mutants of mek-1, jkk-1 and jnk-1 and unc-16 were therefore examined to determine if these mutations affected life span when compared to wild type or to the previously characterized reduction of function mutant of daf-2 (e1370).

Results are shown in FIGS. 3a-d. The daf-2 mutant (e1370), as previously shown, significantly extended life span relative to the N2 control strain. Individual reduction of function mutations in the JNK pathway genes, including unc-16 and mek-1, showed no effect on life span relative to the N2 control. Both the jnk-1 and jkk-1 mutants showed a slight, but statistically significant, decrease in life span. The mean life span of the strains were: wild-type=17.1±3.82 (n=45), jnk-1 (gk7)=13.1±3.5 (n=50), jkk-1(km2)=13.6±2.18 (n=50), mek-1=17.9±4.52 (n=49), unc-16=15.6±3.7 (46). These data are the mean±standard deviation, (n)=total number of animals tested.)

The demonstration that a reduction of function mutation jnk-1 uniquely caused a decrease in mean life span was intriguing, given that jnk-1 and mek-1 mutants are hypersensitive to heavy metals (Villanueva A. et al. (2001) *EMBO J.* 20:5114-5128). These data demonstrated that the correlation between resistance to heavy metal stress and the long-lived phenotype was not strictly true. Alternatively, there may be a redundancy among these genes for life span, and the mkk-4 gene was contributing an effect.

Double Mutant Phenotypes

The introduction of a reduction of function mutation in either jnk-1, unc-16 or jkk-1, in combination with a reduction of function mutation in the insulin-like receptor gene daf-2, led to a striking, synergistic enhancement of the life span extension that was associated with the single daf-2 mutant. The mean and maximum life span of double mutant strains were: daf-2, jnk-1 (48.3, 71), daf-2, jkk-1 (47.5, 71), and daf-2, unc-16 (60.9, 100) (mean life span, maximum life span). The demonstration that mutations in jkk-1 or unc-16, which do not affect life span on their own, showed a striking synergistic effect when placed in combination with another mutation that caused a change in signaling in the insulin pathway (and therefore the activity of DAF-16), was novel and unexpected. This result clearly demonstrated a regulatory role for jnk-1, unc-16 and jkk-1 in aging, and indicated that, in the absence of daf-2, the JNK pathway genes jnk-1, unc-16 and jkk-1 function as negative modulators of lifespan in *C. elegans*.

The introduction of a reduction of function mutation in mek-1 in combination with a reduction of function mutation in daf-2 (e1370) led to a partial suppression of the life span extension associated with the single daf-2 mutant. (daf; mek-1 (25.4, 51) (mean life span, maximum life span)). This result contrasted with that obtained with mutants of the other JNK pathway genes, and showed that mek-1, in the absence of daf-2, acts as a positive modulator of life span.

Example 2

Combined Reduction of Function Mutations in a JNK Pathway Gene (jnk-1, unc-16, jkk-1 or mek-1) and Age-1 Synergistically Enhances Life Span Extension of Age-1 Mutant

*C. elegans* strains were constructed harboring reduction of function mutations in age-1 in combination with a reduction of function mutation in either jnk-1, unc-16, jkk-1 or mek-1. The phenotypes of these mutants were assessed using a standard assay for life span, as described in the Materials and Methods of Example 1, in order to determine whether these JNK pathway genes modulated the life span extension associated with a single age-1 mutant.

Figure 4:
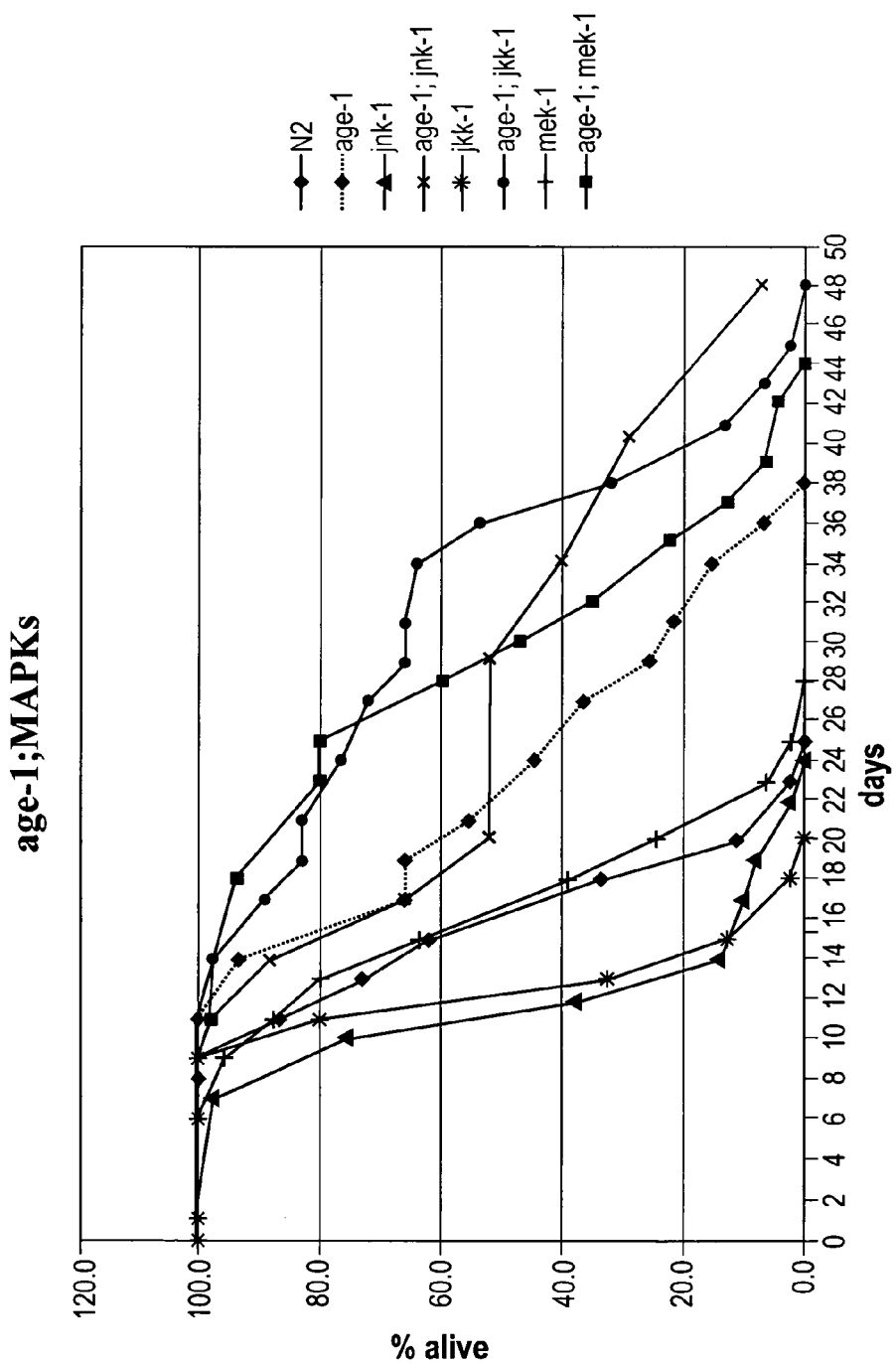
FIG. 4 is a graphical depiction of life span analysis of mutant *C. elegans* strains containing reduction of function mutations jnk-1, unc-16, mek-1 and jkk-1 alone, and in combination with a reduction of function age-1 mutation.
Figure 5:
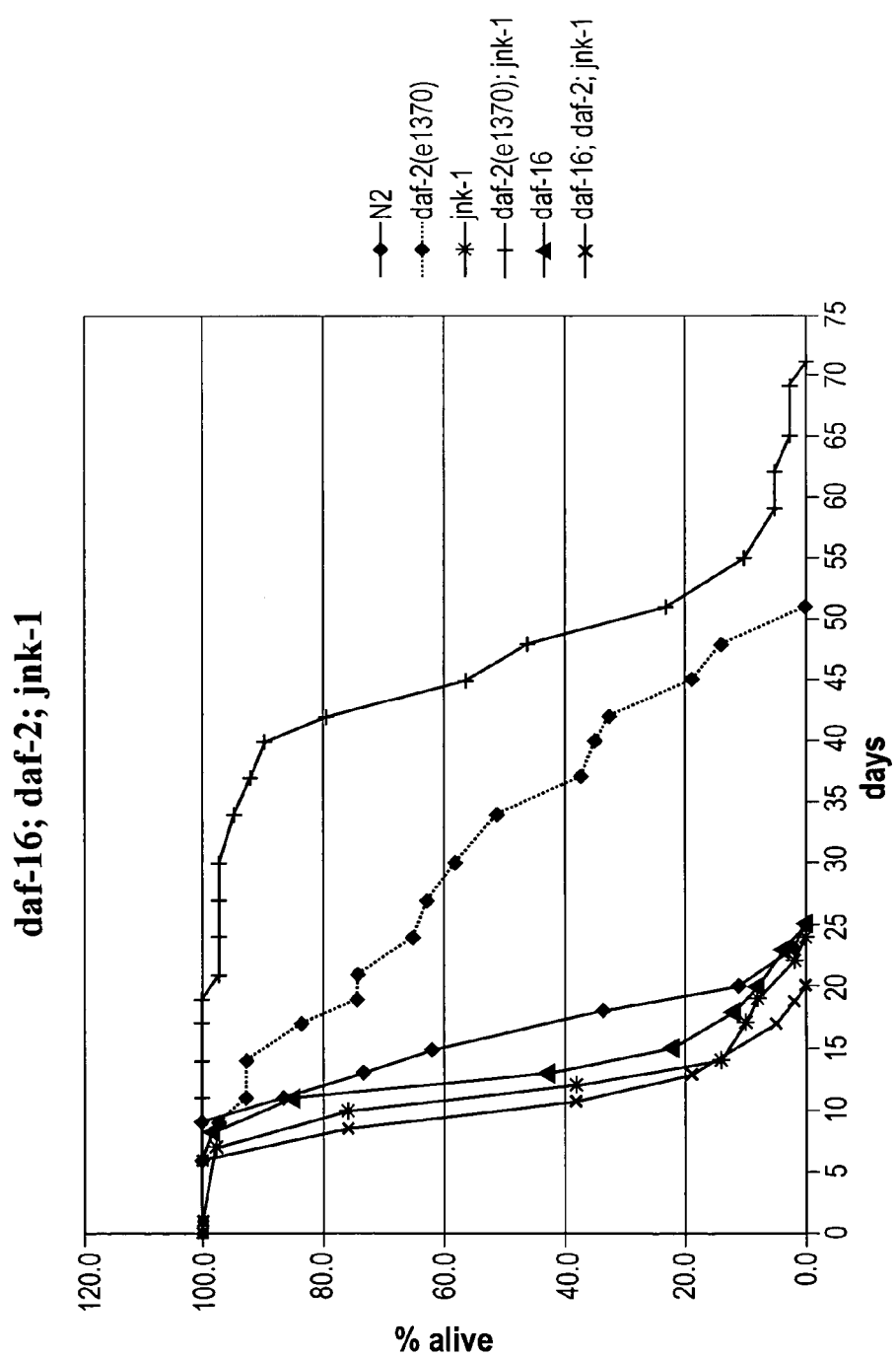
FIG. 5 is a graphical depiction of life span analysis of a double mutant *C. elegans* strain containing reduction of function mutations in daf-2 and jnk-1, and a strain containing this same reduction of function mutations in daf-2 and jnk-1 in combination with a null mutation in daf-16.

Results are shown in FIG. 4. The reduction of function mutation in age-1 significantly extended life span relative to an N2 control strain, as previously described. Single mutants for JNK pathway genes, including unc-16, jkk-1 and mek-1, showed no effect on life span, while the jnk-1 mutant showed a slight, but statistically significant, decrease in life span relative to the N2 control.

The introduction of a reduction of function mutation in jnk-1, unc-16, jkk-1 or mek-1 in combination with a reduction of function mutation in age-1 led to a synergistic enhancement of the life span extension associated with the age-1 single mutant: age-1; jnk-1 (28.9, 48), age-1; jkk-1 (33.7, 48), age-1; mek-1 (30.4, 44), and age-1; unc-16 (22.3, 53) (mean life span, maximum life span). These data further demonstrated a regulatory role for the JNK pathway in aging, and indicate that, in the absence of age-1, each of the JNK pathway genes examined functions as a negative modulator of life span.

Example 3

Enhancement of Life Span Extension in a daf-2/jnk-1 Double Mutant Requires daf-16

To test whether the synergistically enhanced life span extension associated with the double mutant daf-2/jnk-1 was dependent on daf-16, a *C. elegans* strain was constructed that had a null mutation in daf-16 in combination with the reduction of function mutations in jnk-1 and daf-2. The phenotype of this mutant was assessed using a standard assay for life span, as described in the Materials and Methods of Example 1. Life spans were examined to determine whether a mutation in daf-16 modulated the synergistic life span extension associated with the daf-2/jnk-1 mutant.

Results are shown in FIG. 3. The daf-16 mutant showed a slight reduction in life span relative to an N2 control strain, consistent with previous reports. As demonstrated in Example 1, a single jnk-1 mutant exhibited a slight decrease in life span relative to the N2 control, and the double jnk-1/daf-2 mutant showed a synergistic life span extension compared with that of the daf-2 single mutant. Importantly, the introduction of a third mutation in the insulin-signaling gene, daf-16, completely suppressed the synergistic life span extension phenotype of jnk-1/daf-2 to that of the N2 control (daf-16; daf-2, jnk-1 (12.1, 20) (mean life span, maximum life span)). This result demonstrated that jnk-1, like daf-2, requires daf-16 for its life span regulating effects. Taken together, these results placed jnk-1 acting upstream of daf-16 in *C. elegans*.

Example 4

Evaluation of Stress Resistance and Body Movement Coordination in Mutants of Genes in the JNK Pathway (jnk-1, unc-16, jkk-1, mek-1) in Combination with daf-2 or age-1

Reduction of function mutations in jnk-1, jkk-1 and mek-1 result in defects in coordinated body movements and/or resistance to stress, such as heavy metals (Villanueva A. et al. (2001) *EMBO J* 20:5114-5128; Koga M. et al. (2000) *EMBO J* 19:5148-5156; Kawasaki M. et al. (1999) *EMBO J* 18:3604-3615). These defects in coordination are primarily due to the fact that at least jnk-1 and jkk-1 are expressed in both the cell bodies and the axons of most neurons. In order to evaluate resistance to various stresses, including UV, oxidative and heat stress, as well as body movement coordination, *C.*

*elegans* strains harboring a reduction of function mutation in daf-2 or age-1 in combination with a reduction of function mutation in jnk-1, jkk-1, mek-1, unc-16 or mkk-4 are generated as in Examples 1 and 2. Mutants are then examined for stress resistance and the movement phenotype as follows:

UV stress Approximately 30-40 L4~young adult animals are removed from a seeded plate, washed in 1XS-Basal, then transferred to an unseeded NGM plate. Animals are exposed to 40 J/m2 in a Stratalinker 2400 (Stratagene). Animals are removed from the unseeded plate and placed on a seeded one. Life span is calculated from the day of UV treatment. UV treatment often leads to egg laying defects and bagged adults. These animals are censored from life span calculations.

Oxidative Stress

For each strain to be tested, 100 L 1 animals are placed to develop to adulthood on NGM plates containing different concentrations of paraquat (0 mM, 0.2 mM, 0.4 mM, 0.6 mM, and 0.8 mM) (Feng et al. (2001) *Dev. Cell.* 1:1-20). For each strain, worms are monitored each day until 6 days after the first worms become adults. The percentage of worms that reach adulthood is expressed as survival.

Heat Stress

Intrinsic thermotolerance is measured as a percent of a cohort of L4~ young adult worms that survive a near-lethal heat shock. Specifically, 30-40 wild type or mutant adults are placed on a seeded NGM plate and left to lay eggs for 3-4 hours. Adults are removed and eggs are allowed to develop until 3 days past L4 molt. Next, 30-40 rolling adults are placed on a small seeded NGM plate at 35° C. for 24 hours. The worms are then scored for viability.

Body Movement Coordination Assay

Single L4~young adult worm is placed on a seeded NGM plate and body bending per minute is recorded by manual counting under the microscope. The locomotion of worms is observed after 1 min, 10 min, and 60 min by drawing the line on the plate lid along the tracks made by worms.

Example 5

Materials and Methods for Examples 6-9

Construction of *C. Elegans* Strain Overexpressing jnk-1

The jnk-1 genomic sequence, including the promoter region, 3 kb of DNA upstream of the start codon, the entire coding region and 500 bp of the 3'-UTR, was amplified by PCR of N2 genomic DNA (upstream primer 5'-GCGTCCTC-CTGTGCTCACTC (SEQ ID NO:7), and downstream primer 5'-CCCACGACAACTGCTACAAC (SEQ ID NO:8)) After gel purification, a 9.3 kb fragment was injected into N2 animals at 50 ng/μl along with a co-injection marker, pRF4 rol-6, at 100 ng/μl. A stable transgenic line was generated by irradiating with UV at 300 J/m$^2$ in order to integrate extrachromosomal arrays into the chromosome. Several extrachromosomal and integrated lines were established and compared for each experiment.

Strain Construction

To construct double mutant strains overexpressing jnk-1 and containing either a reduction of function mutation in jkk-1, mek-1 or unc-16, or that expressed GFP-tagged DAF-16, the following general approach was used: jnk-1 overexpression hermaphrodites were crossed with males of jkk-1, mek-1, unc-16, or daf-16::GFP, which were obtained by heat shock at 30° C. or which occurred naturally. For individual F2 cross progeny, jnk-1 overexpression was confirmed by roller phenotype or by PCR (upstream primer 5'-ACAGTGGAA-CAGGAGGAGG (SEQ ID NO:9), and downstream primer 5'-ATGCCTATCTGCCTGAGAGC (SEQ ID NO:10)), jkk-1 deletion was confirmed by single worm PCR (upstream primer 5'-AGGAGAAAAGCAAGTTGTCG (SEQ ID NO:11), and downstream primer 5'-GCAGCAGCTTCTCA-CAACAC (SEQ ID NO:12)), mek-1 was confirmed by hypersensitivity to $CuSO_4$, unc-16 was confirmed by unc phenotype, and daf-16::GFP was characterized by GFP signal. A daf-2:daf-16::GFP double mutant was made by crossing daf-2 males with daf-16::GFP hermaphrodites. Approximately 20 putative F1 roller cross progeny were transferred to 25° C. Homozygote daf-2 rollers were selected by dauer phenotype at 25° C. Each double mutant was confirmed again using F3 progeny.

Life Span Analysis

Life span assays were performed at 20° C. using nematode growth medium (NGM) plates containing 0.1 mg/ml of 5'-flourodeoxyuridine (FUDR) to prevent the growth of progeny. Adult hermaphrodites from each strain were grown on NGM plates, allowed to undergo one full generation at 20° C., and L4s or young adults were transferred to FUDR plates. Animals were tapped every 2-3 days and scored as dead when they did not respond to a platinum wire pick. Life span is defined as days that worms are alive after they were transferred to an FUDR plate (day 1). All the lifespan assays were repeated at least three times.

Lifespan Analysis on RNAi Plate

A single colony from each RNAi clone, which expresses double-stranded RNA, was grown in LB broth containing 50 μg/ml ampicillin and 12.5 μg/ml tetracycline until the culture reached an OD=0.5-1.0, and was then seeded onto a NGM plate containing 1 mM isopropylthiogalactoside (IPTG), 50 μg/ml of ampicillin, and 0.1 mg/ml FUDR. Seeded plates were allowed to induce double-stranded RNAi, dried at room temperature overnight, and then stored at 4° C. (as described in *Genome Biology* 2000, 2(1): research 0002.1-0002.10). For each strain, lifespan was examined on an empty RNAi vector plate (HT115 bacteria containing L4440 plasmids) as a control and compared to lifespan on specific RNAi plates.

Visualization of DAF-16 Translocation

DAF-16 translocation was visualized by a GFP microscope (Zeiss, Axioskop 2 plus) equipped with a Hamamtsu C4742-95 digital camera. Images were obtained using OpenLab 3.1.4 software (Improvision).

Stress Assays

For oxidative stress assays, 30~40 young adults were transferred to 96-well plates (5~6 worms/well) containing 40 μl of 150 mM paraquat. Worms were scored for survival every 30 minutes by tapping them with a platinum wire pick. For heat shock assays, 50 young adults were transferred onto NGM plates and kept at 35° C. Worms were scored for survival every hour. Each stress assay was repeated at least 5 times.

Example 6

Overexpression of jnk-1 Extends Lifespan

Single Reduction-of-Function Mutant Phenotypes

Figure 6:
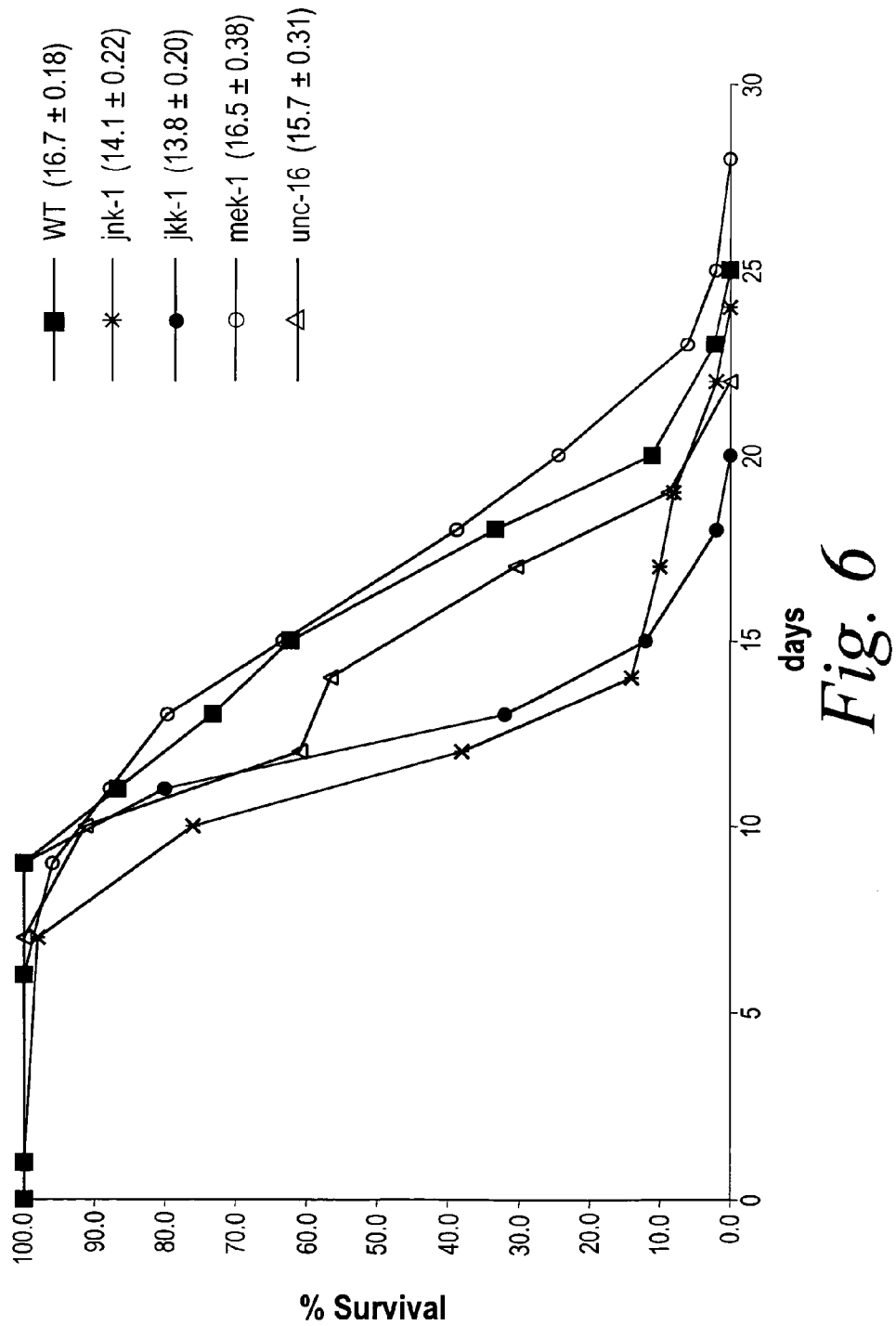
FIG. 6 is a graphical depiction of life span analysis of mutant *C. elegans* strains containing single reduction of function mutations in jnk-1, unc-16, mek-1 and jkk-1.

In similar experiments to those described in Example 1, the life span of single reduction of function mutants of mek-1, jkk-1, jnk-1 and unc-16 were examined for the effects of these mutations on life span as compared to wild type. The strains, construction and characterization thereof, and life span analysis were as set forth in Example 1. Results, as shown in FIG. 6, demonstrate that mek-1 and unc-16 mutant showed little or no effect on life span, while the jnk-1 and jkk-1 mutants showed a statistically significant decrease in life span. The mean life span of the strains were: wild-type=16.7±0.18, mek-1=16.5±0.38, unc-16=15.7±0.31, jnk-1(gk7)=14.1±0.22, jkk-1(km2)=13.8±0.20. These data are the mean±standard error. These results are consistent with those found in Example 1.

Overexpression of jnk-1 Extends Lifespan

A 9.3 kb region of genomic DNA spanning the jnk-1 gene, including 3 kb of the promoter region and 500 bp of the 3'-UTR (depicted in FIG. 7A), was amplified by PCR. This DNA was then injected into the gonads of wild type worms (N2) along with the coinjection marker, rol-6, as described above. By using this approach, a jnk-1 overexression transgenic line was created that contained extra copies of the jnk-1 gene, as confirmed by single-worm PCR analysis (FIG. 7B). The expression level of JNK-1 in this transgenic line was examined using RT-PCR and the results are presented in FIG. 7C. These results demonstrated that JNK-1 expression was elevated by approximately 10-fold.

Figure 8:
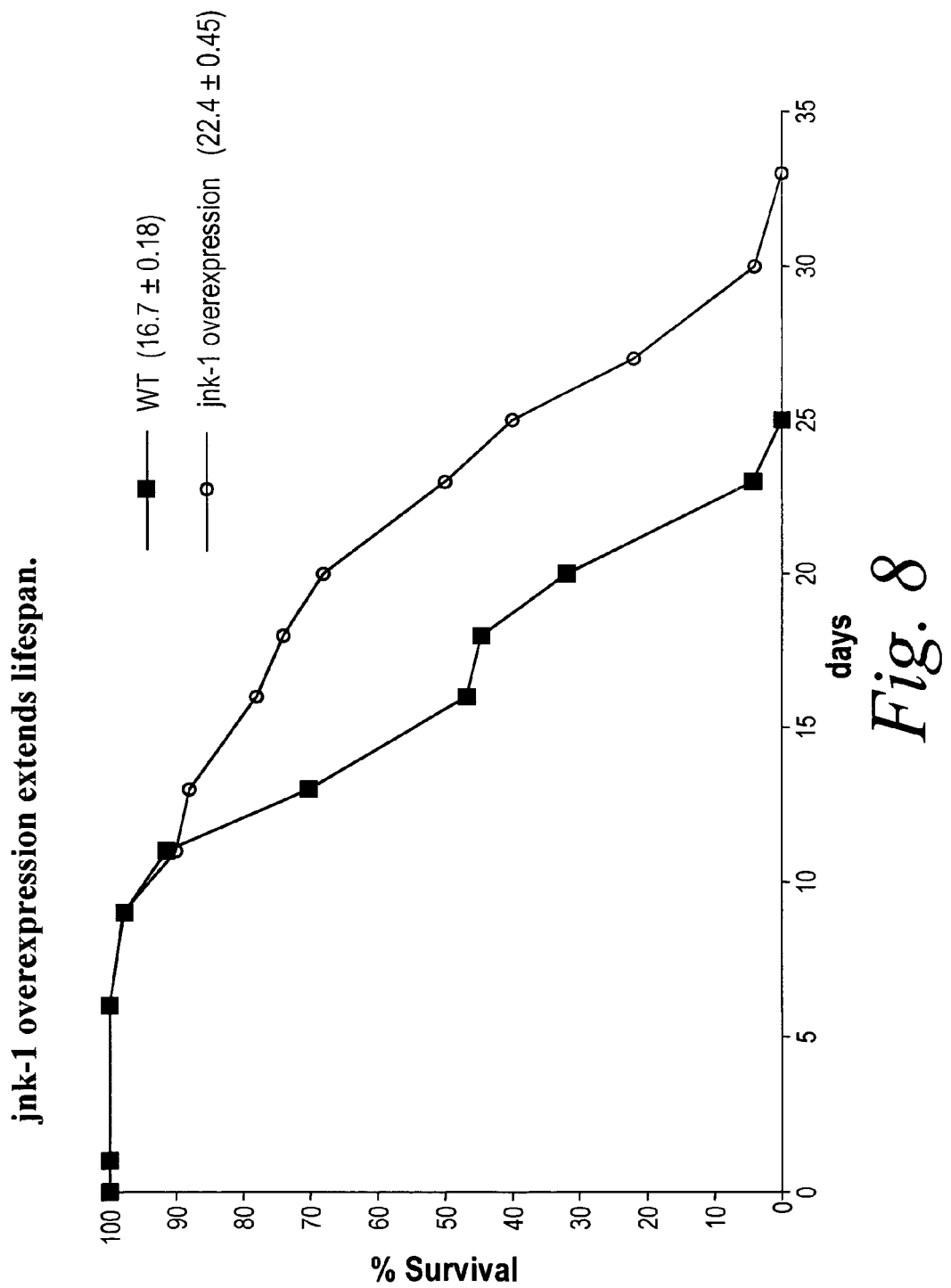
FIG. 8 is a graphical depiction of life span analysis of a jnk-1 overexpression transgenic *C. elegans* strain.

The phenotype of the jnk-1 overexpression strain was assessed using a standard assay for life span to test whether overexpression of jnk-1 modulates life span. As shown in FIG. 8, overexpression of jnk-1 increased life span significantly. The mean life span of the strains were: wild-type=16.7±0.18, jnk-1 overexpression=22.4±0.45. These data are the mean±standard error. Taken together with results from the reduction of function mutants, these results indicated that the JNK signaling pathway is required to maintain the normal lifespan (as demonstrated in the present Example and in Example 1) while additional JNK signaling can extend lifespan. These results suggested that the JNK signaling pathway regulates lifespan in a dose-dependent manner in *C. elegans*.

Example 7

DAF-16 is Required for Lifespan Extension by jnk-1 Overexpression and is Localized to the Nucleus in a jnk-1 Overexpression Strain The next question addressed was whether daf-16 was required for the observed lifespan extension upon overexpression of jnk-1. To address this question, the lifespan of the jnk-1 overexpression strain was measured on a daf-16 RNAi plate or on an empty RNAi vector plate as control (L4440) (as described in *Nature Genetics* 2003, 33:40-48). The results of this analysis, which are presented in FIG. 9, revealed that the lifespan extension associated with jnk-1 overexpression was completely suppressed by daf-16 RNAi. These results indicated that daf-16 is required for the lifespan extension associated with jnk-1 overexpression.

The translocation of DAF-16 from the cytoplasm into the nucleus is a key event in lifespan regulation. Given that the lifespan extension exhibited upon jnk-1 overexpression required daf-16, it was possible that jnk-1 overexpression mediated its effect on lifespan by modulating DAF-16 localization. To examine localization of DAF-16 in the jnk-1 overexpression strain, a jnk-1 overexpression worm was crossed with a daf-16::GFP strain, and DAF-16 translocation was visualized using a GFP microscope. The results of this experiment are presented in FIGS. 10A-C. In the wild-type strain, DAF-16 was localized predominantly in the cytosol (FIG. 10A), while in the daf-2 mutant strain DAF-16 was translocated to the nucleus (FIG. 10B), as previously described. Strikingly, DAF-16 was similarly localized to the nucleus in a jnk-1 overexpression strain (FIG. 10C). These results revealed a novel mechanism by which translocation of DAF-16 is regulated, and suggested that jnk-1 overexpression extends lifespan by localizing DAF-16 into the nucleus.

Example 8

Figure 11A:
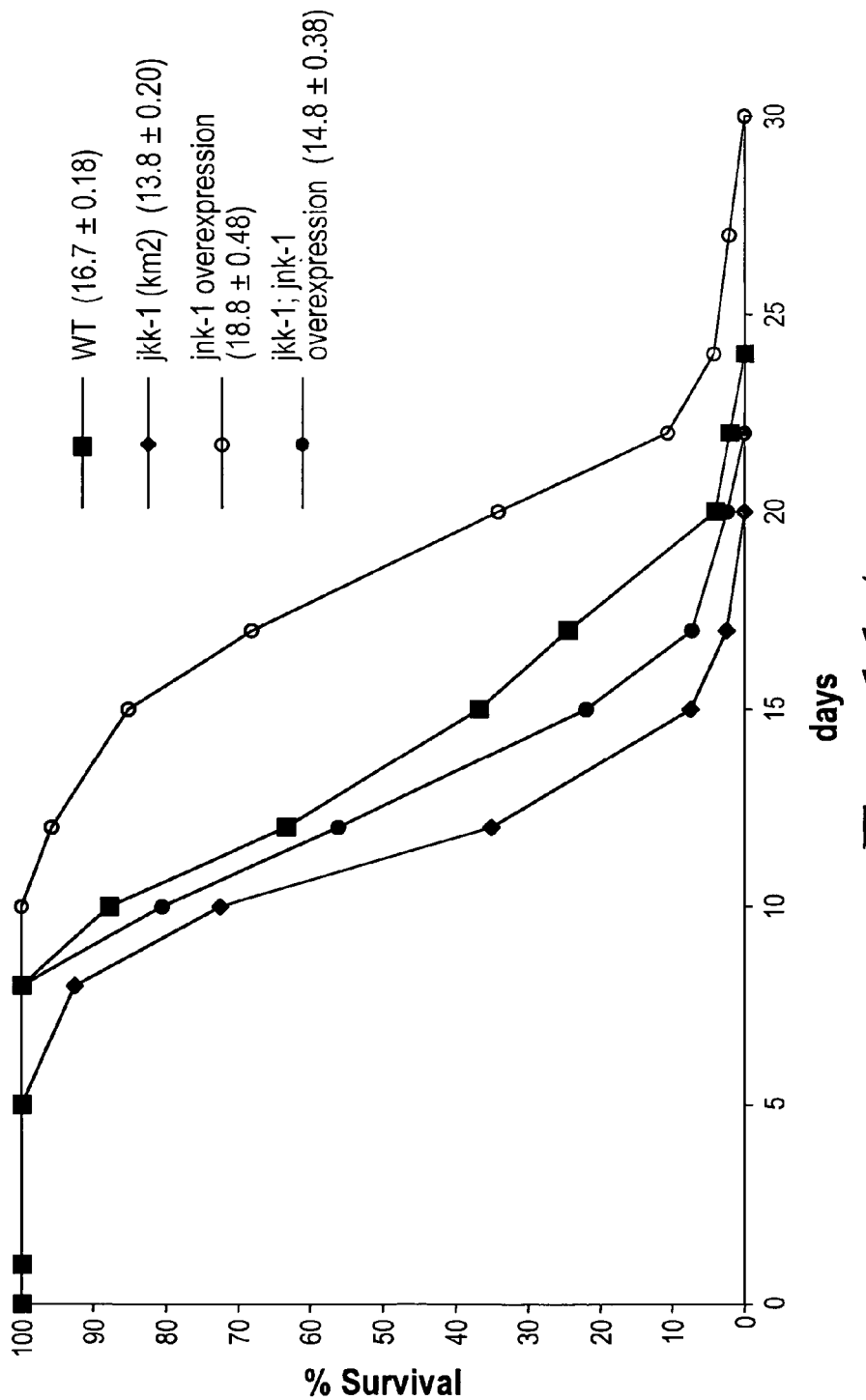
FIG. 11A is a graphical depiction of life span analysis of a mutant *C. elegans* strain containing a reduction of function mutation in jkk-1 alone, and in combination with overexpression of jnk-1.
Figure 11B:
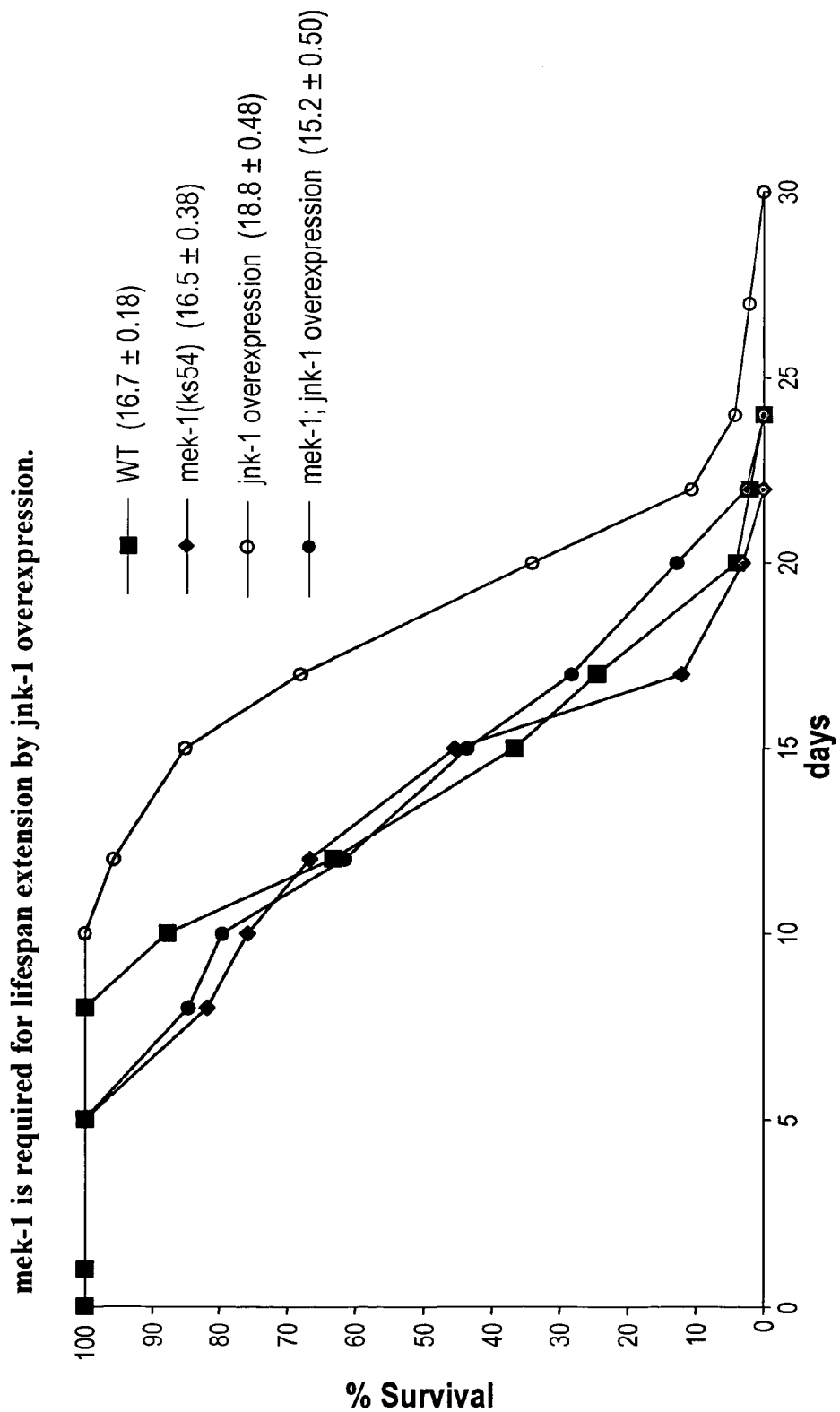
FIG. 11B is a graphical depiction of life span analysis of a mutant *C. elegans* strain containing a reduction of function mutation in mek-1 alone, and in combination with overexpression of jnk-1.
Figure 11C:
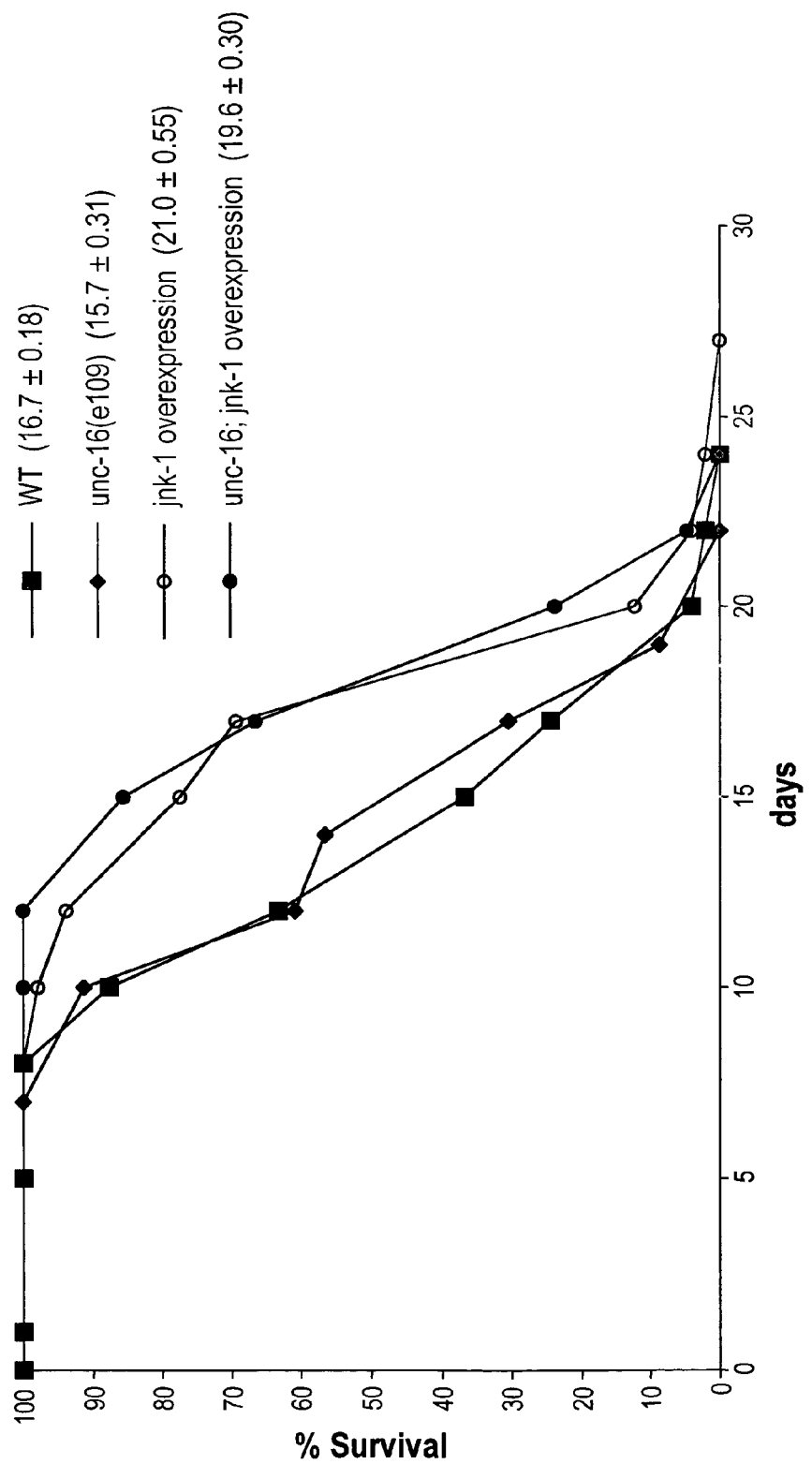
FIG. 11C is a graphical depiction of life span analysis of a mutant *C. elegans* strain containing a reduction of function mutation in unc-16 alone, and in combination with overexpression of jnk-1.

Upstream Kinases jkk-1 and mek-1, but not unc-16, are Required for Life Span Extension by jnk-1 Overexpression The next question addressed was whether the kinases that act upstream of jnk-1, including jkk-1, mek-1, or unc-16, are required for the observed lifespan extension upon overexpression of jnk-1. To address this question, a jnk-1 overexpression worm was crossed with *C. elegans* reduction of function mutants for other components in JNK signaling pathway, including jkk-1, mek-1, and unc-16, and the life span of these strains were analyzed. Results of these experiments are presented in FIGS. 11A-C. Lifespan extension by jnk-1 overexpression was completely suppressed by a reduction of function mutation in jkk-1 (FIG. 11A). The mean life span of the strains were: wild-type=16.7±0.18, jkk-1(km2)=13.8±0.20, jnk-1 overexpression=18.8±0.48, jkk-1, jnk-1 overexpression=14.8±0.38 (mean±standard error). Similarly, lifespan extension by jnk-1 overexpression was completely suppressed by a reduction of function mutation in mek-1 (FIG. 11B). The mean life span of the strains were: wild-type=16.7±0.18, mek-1(ks54)=16.5±0.38, jnk-1 overexpression=18.8±0.48, mek-1, jnk-1 overexpression=15.2±0.50 (mean±standard error). In contrast, life span extension by jnk-1 overexpression was not affected by a mutation in unc-16 (FIG. 11C). The mean life span of the strains were: wild-type=16.7±0.18, unc-16(e109)=15.7±0.31, jnk-1 overexpression=21.0±0.55, unc-16, jnk-1 overexpression=19.6±0.30 (mean±standard error). These results indicate that jkk-1 and mek-1, but not unc-16, are required for lifespan extension by jnk-1 overexpression.

Example 9

Overexpression of jnk-1 in *C. Elegans* Confers Resistant to Stress

Figure 12A:
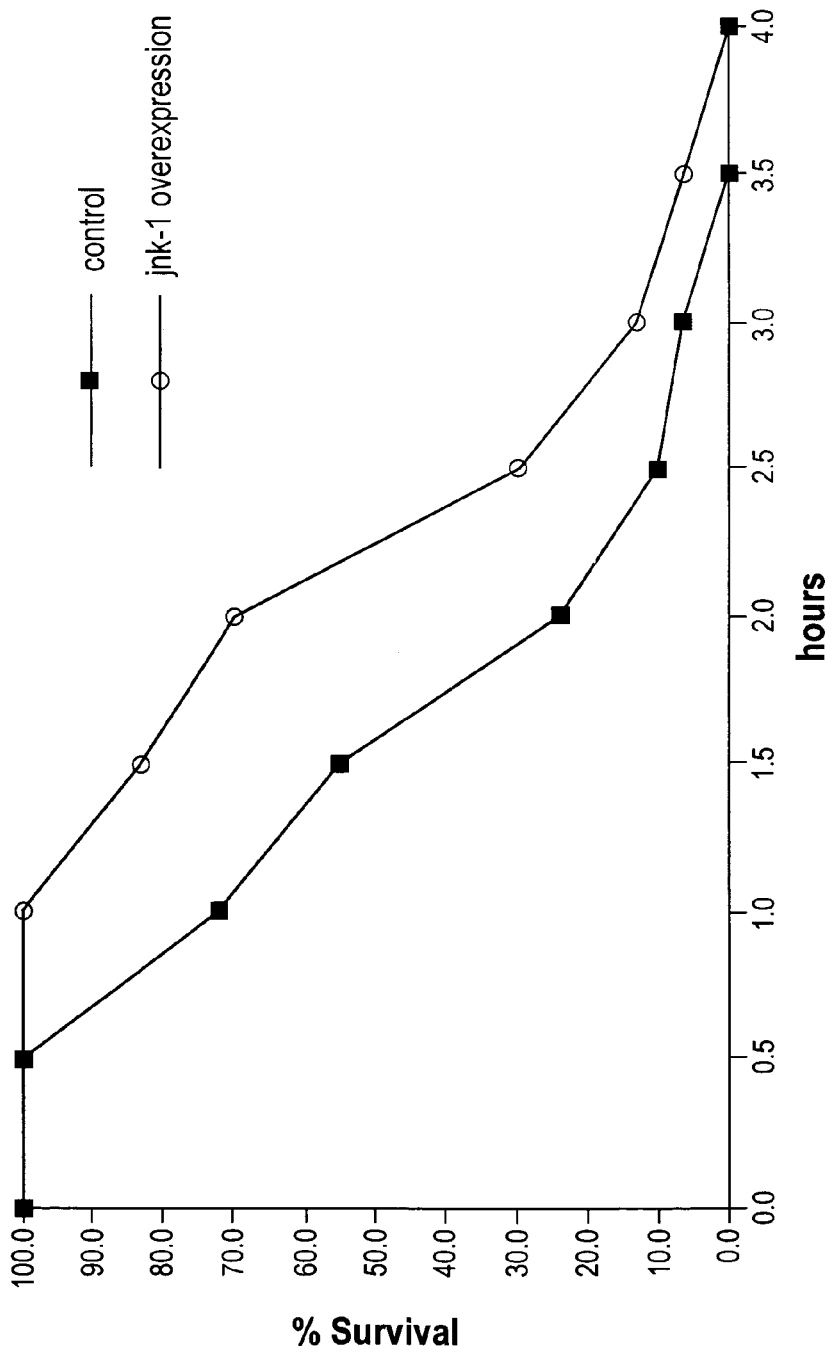
FIG. 12A is a graphical depiction of oxidative stress analysis of a jnk-1 overexpression *C. elegans* strain.

A jnk-1 overexpression worm was challenged with 150 mM of paraquat or exposed to heat shock at 35° C., and the worms were then scored for survival every 30 minutes or 1 hour, respectively. The results of these experiments, as presented in FIGS. 12A-B, demonstrate that a jnk-1 overexpression *C. elegans* strain was significantly resistant to both heavy metal stress (FIG. 12A) and to heat shock stress (FIG. 12B). These results suggest that lifespan extension by jnk-1 overexpression is due to stress resistance.

Summary of Examples 6-9

Taken together, the results of the present invention suggest that the JNK signaling pathway can regulate lifespan by modulating nuclear translocation of DAF-16 (model as depicted in FIG. 13). In particular, the results of the present invention suggest that the JNK signaling pathway is important to maintain normal lifespan and can extend lifespan when it is activated. This extension of lifespan appears to be mediated by both the jkk-1 and mek-1 upstream kinases. Moreover, the results presented herein indicate that when the JNK signaling pathway is activated, jnk-1 localizes DAF-16 into the nucleus where it enhances the expression of stress resistant genes, thereby conferring stress resistance and extending life span

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

1. Villanueva, A., Lozano, J., Morales, A., Lin, X., Deng, X., Hengartner, M. O. & Kolesnick, R. N. jkk-1 and mek-1 regulate body movement coordination and response to heavy metals through jnk-1 in *Caenorhabditis elegans*. *EMBO J* 20, 5114-5128 (2001).
2. Morris, J. Z., Tissenbaum, H. A. & Ruvkun, G. A phosphatidylinositol-3-OH kinase family member regulating longevity and diapause in *Caenorhabditis elegans*. *Nature* 382, 536-539 (1996).
3. Kimura, K., Tissenbaum, H. A., Liu, Y. & Ruvkun, G. The daf-2 insulin receptor family member regulates longevity and diapause in *Caenorhabditis elegans*. *Science* 277, 942-946 (1997).
4. Ogg, S., Paradis, S., Gottlieb, S., Patterson, G. I., Lee, L., Tissenbaum, H. A. & Ruvkun, G. The Fork head transcription factor DAF-16 transduces insulin-like metabolic and longevity signals in *C. elegans*. *Nature* 389, 994-9(1997).
5. Tissenbaum, H. A. & Ruvkun, G. An insulin-like signaling pathway affects both longevity and reproduction in *Caenorhabditis elegans*. *Genetics* 148, 703-717 (1998).
6. Cassada, R. C. & Russell, R. The dauer larva, a post-embryonic developmental variant of the nematode *Caenorhabditis elegans*. *Developmental Biology* 46, 326-342 (1975).
7. Klass, M. R. & Hirsh, D. I. Nonaging developmental variant of *C. elegans*. *Nature* 260, 523-525 (1976).
8. Riddle, D. L. & Albert, P. S. in *C. elegans* II (eds. Riddle, D. L., Blumenthal, T., Meyer, B. J. & Priess, J. R.) 739-768 (Cold Spring Harbor Laboratory Press, 1997).
9. Pierce, S. B., Costa, M., Wisotzkey, R., Devadhar, S., Homburger, S. A., Buchman, A. R., Ferguson, K. C., Heller, J., Platt, D. M., Pasquinelli, A. A., Liu, L. X., Doberstein, S. K. & Ruvkun, G. Regulation of DAF-2 receptor signaling by human insulin and ins-1, a member of the unusually large and diverse *C. elegans* insulin gene family. *Genes and Development* 15, 672-686 (2001).
10. Gregoire, F. M., Chomiki, N., Kachinskas, D. & Warden, C. H. Cloning and developmental regulation of a novel member of the insulin-like family in *Caenorhabditis elegans*. *Biochem Biophys Res Commun* 249 385-390 (1998).
11. Kido, Y., Nakae, J. & Accili, D. The Insulin receptor and its cellular targets. *Journal of Clinical Endocrinology and Metabolism* 86, 972-979 (2001).
12. Alessi, D. R. & Downes, C. P. The role of PI 3-kinase in insulin action. *Biochim Biophys Acta* 1436 151-164 (1998).
13. Lithgow, G. J., White, T. M., Hinerfeld, D. A. & Johnson, T. E. Thermotolerance of a long-lived mutant of *Caenorhabditis elegans*. *J. Gerontol.* 49, B270-276 (1994).
14. Lithgow, G. J., White, T. M., Melov, S. & Johnson, T. E. Thermotolerance and extended life-span conferred by single-gene mutations and induced by thermal stress. *Proc NatlAcadSci USA* 92, 7540-4 (1995).
15. Murakami, S. & Johnson, T. E. A genetic pathway conferring life extension and resistance to UV stress in *Caenorhabditis elegans*. *Genetics* 143, 1207-1218 (1996).
16. Honda, Y. & Honda, S. The daf-2 gene network for longevity regulates oxidative stress resistance and Mn-superoxide dismutase gene expression in *Caenorhabditis elegans*. *FASED J* 13, 1385-1393 (1999).
17. Baryste, D., Lovejoy, D. A. & Lithgow, G. J. Longevity and heavy metal resistance in daf-2 and age-1 long-lived mutants of *Caenorhabditis elegans*. *FasEB J* 15, 627-634 (2001).
18. Friedman, D. B. & Johnson, T. E. A mutation in the age-1 gene in *Caenorhabditis elegans* lengthens life and reduces hermaphrodite fertility. *Genetics* 118, 75-86 (1988).
19. Klass, M. R. A method for the isolation of longevity mutants in the nematode *Caenorhabditis elegans* and initial results. *Mechanisms of Ageing and Dev.* 22, 279-286 (1983).
20. Paradis, S. & Ruvkun, G. *Caenorhabditis elegans* Akt/PKB transduces insulin receptor-like signals from AGE-1 PI3 kinase to the DAF-16 transcription factor. *Genes and Development* 12, 2488-2498 (1998).
21. Paradis, S., Ailion, M., Toker, A., Thomas, J. H. & Ruvkun, G. A PDK1 homolog is necessary and sufficient to transduce AGE-1 PI3 kinase signals that regulate diapause in *Caenorhabditis elegans*. *Genes Dev* 13, 1438-1452 (1999).
22. Rouault, J. P., Kuwabara, P. E., Sinilnikova, O. M., Duret, L., Thierry-Mieg, D. & Billaud, M. Regulation of dauer larva development in *Caenorhabditis elegans* by daf-18, a homologue of the tumour suppressor PTEN. *Current Biology* 9, 329-332 (1999).
23. Ogg, S. & Ruvkun, G. The *C. elegans* PTEN homolog, DAF-18, acts in the insulin receptor-Like metabolic signaling pathway. *Molecular Cell* 2, 887-893 (1998).
24. Mihaylova, V. T., Borland, C. Z., Manjarrez, L., Stern, M. J. & Sun, H. The PTEN tumor suppressor homolog in *Caenorhabditis elegans* regulates longevity and dauer formation in an insulin receptor-Like signaling pathway. *Proc NatlAcadSci USA* 96, 7427-7432 (1999).
25. Gil, E. B., Malone Link, E., Liu, L. X., Johnson, C. D. & Lees, J. A. Regulation of the insulin-Like developmental pathway of *Caenorhabditis elegans* by a homolog of the PTEN tumor suppressor gene. *Proc NatlAcadSci USA* 96, 2925-2930 (1999).
26. Maehama, T. & Dixon, J. E. The tumor suppressor, PTEN/MMAC1, dephosphorylates the lipid second messenger, phosphatidylinositol 3,4,5-trisphosphate. *Journal of Biological Chemistry* 273, 13375-13378 (1998).
27. Lin, K., Dorman, J. B., Rodan, A. & Kenyon, C. daf-16: An HNF-3/forkhead family member that can function to double the life-span of *Caenorhabditis elegans*. *Science* 278, 1319-1322 (1997).
28. Kenyon, C. in *C. elegans* II (eds. Riddle, D. L., Blumenthal, T., Meyer, B. J. & Priess, J. R.) 791-813 (Cold Spring Harbor Lab. Press, Plainview, N.Y., 1997).
29. Gems, D., Sutton, A. J., Sundermeyer, M. L., Albert, P. S., King, K. V., Edgley, M. L., Larsen, P. L. & Riddle, D. L. Two pleiotropic classes of daf-2 mutation affect larval arrest, adult behavior, reproduction and longevity in *Caenorhabditis elegans*. *Genetics* 150, 129-155 (1998).
30. Sone, H., Suzuki, H., Takahashi, A. & N., Y. Disease model: hyperinsulinemia and insulin resistance. Part A—targeted disruption of insulin signaling or glucose transport. *Trends in Molecular Medicine* 7, 320-322 (2001).
31. Ip, T. Y. & Davis, R. J. Signal transduction by the c-Jun N-terminal kinase (JNK)—from inflammation to development. *Current Opinion in Cell Biology* 10, 205-219 (1998).

32. Weston, C. R. & Davis, R. J. The JNK signal tranduction pathway. *Current Opinion in Genetics and Development* 12, 14-21 (2002).
33. Aguirre, V., Uchida, T., Yenush, L, Davis, R. & White, M. F. The c-Jun $NH_2$-ierminal kinase promotes insulin resistance during association with insulin receptor substrate-1 and phosphorylation of $Ser^{307}$. *Journal of Biological Chemistry* 275, 9047-9054 (2000).
34. Koga, M., Zwaal, R., Guan, K.-L., Avery, L. & Ohshima, Y. A *Caenorhabditis elegans* MAP kinase kinase, MEK-1, is involved in stress responses. *EMBO J* 19, 5148-5156 (2000).
35. Kawasaki, M., Hisamoto, N., lino, Y., Yamamoto, M., Ninomiya-Tsuji, J. & Matsumoto, K. A *Caenorhabditis elegans* INK signal transduction pathway regulates coordinated movement via type-D GABAergic motor neurons. *EMBO J* 18, 3604-3615 (1999).
36. Tissenbaum, H. A. & Guarente, L. Model systems as a guide to mammalian aging. *Developmental Cell* 2 9-19 (2002).
37. Byrd, D. T., Kawasaki, M., Walcoff, M., Hisamoto, N., Matsumoto, K. & Jin, Y. UNC-16, a JNK-signaling scaffold protein regulates vesicle transport in *C. elegans*. *Neuron* 32, 787-800 (2001).
38. Yasuda, J., Whitmarsh, A. J., Cavanaugh, J., Sharma, M. & Davis, R. J. The IIP group of mitogen-activated protein kinase scaffold proteins. *Molecular and Cellular Biology* 19, 7245-7254 (1999).
39. Dlakic, M. A new family of putative insulin receptor-like proteins in *C. elegans*. Current Biology (2002) 12(5) R155-R157.
40. Wokow C. A., Munoz M. J., Riddle D. L. & Ruvkun G. Insulin receptor substrate and p55 orthologous adaptor proteins function in the *Caenorhabditis elegans* daf-1/Insulin-like signaling pathway (2002) *J. Biol. Chem.* 277 (51): 49591-49597.
41. Apfeld J. & Kenyon C., Cell nonautonomy of *C. elegans* daf-2 function in the regulation of diapause and life span (1998) Cell 95: 199-210
42. Feng J., Bussiere F., Hekimi S. Mitochondrial electron transport is a key determinant of life span in *Caenorhabditis elegans*. 2001 Cell 1:1-20.
43. Holzenberger M. Dupont J., Ducos B., Leneuve P., Geloen A., Even P. C., Cervera P., Le Bouc Y., IGF-1 receptor regulates lifespan and resistance to oxidative stress in mice. (2002) Nature, Dec. 4, in press.
44. Jia K., Albert P. S. and Riddle, D. L., DAF-9, a cytochrome P450 regulating *C. elegans* larval development and adult longevity. (2002) Development 129:221-231.
45. Gerisch B., Weitzel C., Kober-Eisermann C., Rottiers V. and Antebi A. A hormonal signaling pathway influencing *C. elegans* metabolism, reproductive development, and life span. (2001) Dev. Cell., 1(6):841-51.

---

What is claimed:

1. A method for identifying an agent capable of increasing lifespan, comprising:
contacting an organism selected from the group consisting of nematodes, yeast and *Drosophila* with a test agent;
assaying for the ability of the test agent to increase the activity of c-jun N-terminal kinase-1 (JNK-1) and localization of DAF-16 to the nucleus when compared to a suitable control to which no agent is added; and
selecting an agent that increases JNK-1 activity and nuclear localization of DAF-16;
to thereby identify an agent capable of increasing lifespan.

2. The method of claim 1, wherein the organism is a nematode.

3. The method of claim 2, wherein the nematode is *C. elegans*.

4. The method of claim 2, wherein the nematode is a parasitic nematode.

5. The method of claim 1, further comprising assaying for the ability of the test agent to affect a detectable phenotype selected from the group consisting of lifespan and stress resistance in said organisms as compared to a suitable control.

6. The method of claim 5, wherein said stress is selected from the group consisting of oxidative stress, ultraviolet (UV) stress, hypoxic stress, heavy metal stress and heat stress.

7. The method of claim 1, wherein the organism has decreased JNK-1 activity.

8. The method of claim 1, wherein the organism has a deregulated insulin signaling pathway molecule selected from the group consisting of DAF-2, AAP-1, IRS, AGE-1, PDK-1, AKT-1, AKT-2 and DAF-18, or orthologue thereof.

9. The method of claim 1, wherein JNK-1 activity is determined by measuring the phosphorylation of JNK-1.

10. The method of claim 1, wherein JNK-1 activity is determined by measuring the kinase activity of JNK-1.

* * * * *

UNITED STATES PATENT AND TRADEMARK OFFICE
CERTIFICATE OF CORRECTION

| | | |
|---|---|---|
| PATENT NO. | : 7,858,327 B2 | |
| APPLICATION NO. | : 10/746910 | |
| DATED | : December 28, 2010 | |
| INVENTOR(S) | : Heidi A. Tissenbaum et al. | |

It is certified that error appears in the above-identified patent and that said Letters Patent is hereby corrected as shown below:

In the Specification:

Please replace the paragraph at column 1, lines 14-19 with the following paragraph:

--GOVERNMENT RIGHTS AS TO FEDERALLY SPONSORED RESEARCH

This invention was made with Government support under grant no. DK032520 awarded by the National Institutes of Health. The Government has certain rights in the invention.--

Signed and Sealed this
Twenty-first Day of June, 2011

David J. Kappos
*Director of the United States Patent and Trademark Office*

```
SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
acagtggaac aggaggagga                                              20

<210> SEQ ID NO 2
<211> LENGTH: 20
<212> TYPE: DNA
<213> ORGANISM: Artificial Sequence
<220> FEATURE:
<223> OTHER INFORMATION: oligonucleotide

<400> SEQUENCE: 2
atgcctatct gcctgagagc                                              20

<210> SEQ ID NO 3
<211> LENGTH: 20
<212> TYPE: DNA
<213> ORGANISM: Artificial Sequence
<220> FEATURE:
<223> OTHER INFORMATION: oligonucleotide

<400> SEQUENCE: 3
aggagaaaag caagttgtcg                                              20

<210> SEQ ID NO 4
<211> LENGTH: 19
```

```
<212> TYPE: DNA
<213> ORGANISM: Artificial Sequence
<220> FEATURE:
<223> OTHER INFORMATION: oligonucleotide

<400> SEQUENCE: 4
gcagcagctt tcacaacac                                              19

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
caatgagcaa tgtggacagc                                             20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide

<400> SEQUENCE: 6
ccgtctggtc gttgtctttt                                             20

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
gcgtcctcct gtgctcactc                                             20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
cccacgacaa ctgctacaac                                             20

<210> SEQ ID NO 9
<211> LENGTH: 19
<212> TYPE: DNA
<213> ORGANISM: Artificial Sequence
<220> FEATURE:
<223> OTHER INFORMATION: oligonucleotide

<400> SEQUENCE: 9
acagtggaac aggaggagg                                              19

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
```

-continued

```
atgcctatct gcctgagagc                                          20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
aggagaaaag caagttgtcg                                          20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
gcagcagctt ctcacaacac                                          20
```